(12) United States Patent
Sina Raja et al.

(10) Patent No.: US 11,918,191 B2
(45) Date of Patent: *Mar. 5, 2024

(54) DEVICES AND METHODS FOR AIDING CONCEPTION

(71) Applicant: Hannah Life Technologies PTE, Ltd., Singapore (SG)

(72) Inventors: Prusothman Sina Raja, Singapore (SG); Chee Keong Tee, Singapore (SG); Vivek Murali, Singapore (SG); Zongyuan Xu, Singapore (SG); Shruthi Pandi Chelvam, Singapore (SG)

(73) Assignee: HANNAH LIFE TECHNOLOGIES PTE, LTD., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/746,083

(22) Filed: May 17, 2022

(65) Prior Publication Data

US 2023/0048673 A1      Feb. 16, 2023

Related U.S. Application Data

(63) Continuation of application No. 17/025,680, filed on Sep. 18, 2020, now Pat. No. 11,357,481.
(Continued)

(51) Int. Cl.
*A61B 90/00*     (2016.01)
*A61B 10/00*     (2006.01)
*A61B 17/425*    (2006.01)

(52) U.S. Cl.
CPC .......... *A61B 10/0058* (2013.01); *A61B 90/03* (2016.02); *A61B 17/425* (2013.01); *A61B 2560/04* (2013.01)

(58) Field of Classification Search
CPC ........ A61B 10/0058; A61B 17/425–43; A61D 19/00–028; A61F 5/453
See application file for complete search history.

(56) References Cited

U.S. PATENT DOCUMENTS 2,855,932 A    10/1958  Stubbs
3,037,508 A     6/1962  Friedman
(Continued)

FOREIGN PATENT DOCUMENTS

DE    202019100591    3/2019
FR       2787022      6/2000
(Continued)

OTHER PUBLICATIONS

How The Stork OTC Works. (2019). Retrieved from: https://www.storkotc.com/how-it-works/.
(Continued)

*Primary Examiner* — Thaddeus B Cox
(74) *Attorney, Agent, or Firm* — FINNEGAN, HENDERSON, FARABOW, GARRETT & DUNNER LLP

(57) ABSTRACT

A conception aid for assisting in natural conception may include a platform configured for placement in a vaginal canal, wherein the platform comprises one or more capturing elements configured to collect semen. A method of aiding conception may include providing a conception aid device including one or more capturing elements, collecting semen with the one or more capturing elements wherein the one or more capturing elements is configured to contain the collected semen on the device, and positioning the device in a vaginal canal.

21 Claims, 32 Drawing Sheets

Related U.S. Application Data

(60) Provisional application No. 63/017,291, filed on Apr. 29, 2020.

(56) References Cited

U.S. PATENT DOCUMENTS

| | | |
|---|---|---|
| 5,857,959 A | 1/1999 | La Vean et al. |
| 6,230,709 B1 | 5/2001 | LaVean |
| 10,159,510 B2 | 12/2018 | Souther et al. |
| 2007/0256691 A1 | 11/2007 | Oqram et al. |
| 2008/0242919 A1 | 10/2008 | La Vean |
| 2009/0090369 A1 | 4/2009 | Attila |
| 2011/0270127 A1 | 11/2011 | Vered et al. |
| 2012/0029270 A1 | 2/2012 | Stuart |
| 2014/0163437 A1 | 6/2014 | Mack et al. |
| 2015/0313638 A1 | 11/2015 | Rosenberg |
| 2016/0228150 A1 | 8/2016 | Pilgrim |
| 2016/0374724 A1 | 12/2016 | Wren |
| 2018/0338779 A1 | 11/2018 | Haeri |
| 2019/0336167 A1 | 11/2019 | La Vean |
| 2020/0015854 A1 | 1/2020 | Jacoby |
| 2020/0054868 A1 | 2/2020 | Garcia |
| 2021/0267640 A1* | 9/2021 | Stal .................. A61B 17/43 |

FOREIGN PATENT DOCUMENTS

| | | |
|---|---|---|
| JP | 2007296300 | 11/2007 |
| WO | WO-2014/049620 | 4/2014 |

OTHER PUBLICATIONS

PCT/IB2020/058747. Invitation to Pay Additional Fees, dated Dec. 8, 2020. 13 pages.

* cited by examiner

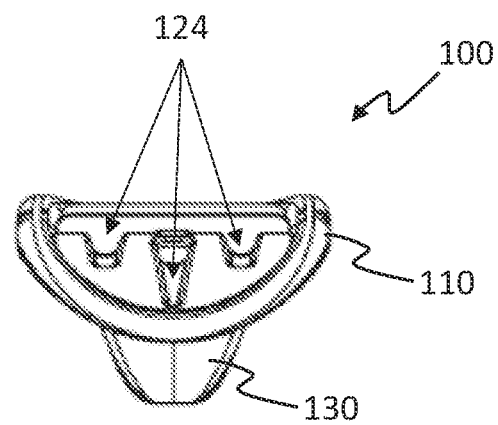
FIG. 1D
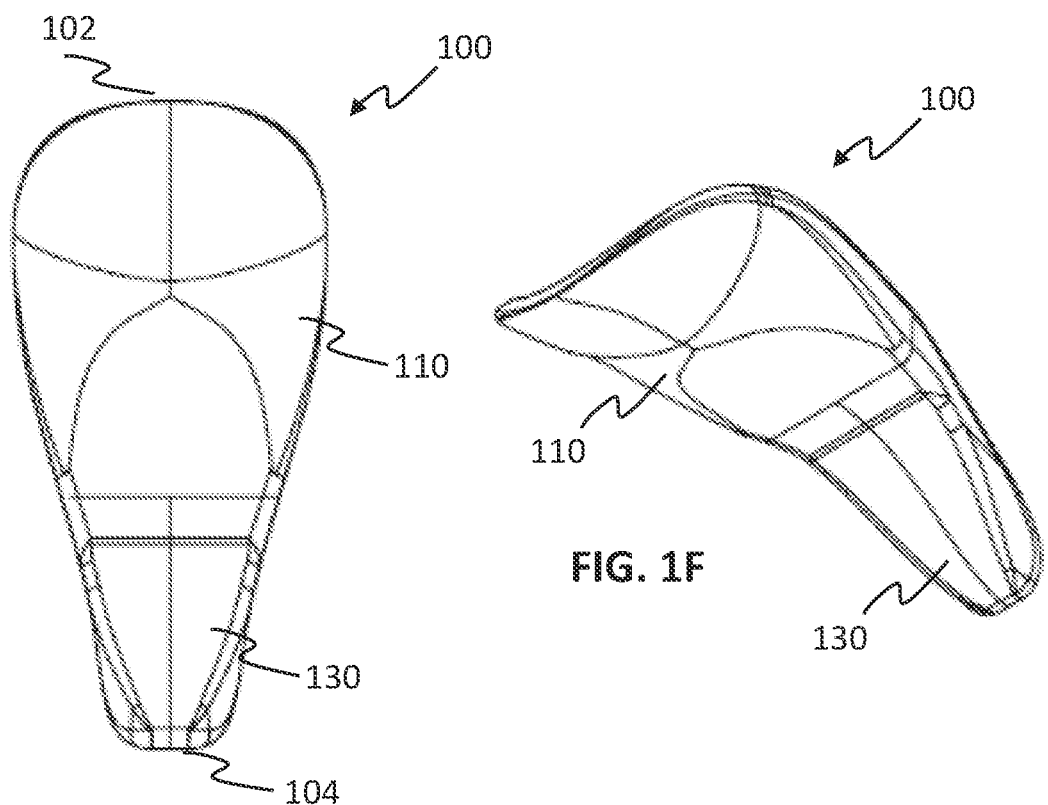
FIG. 1E
FIG. 1F

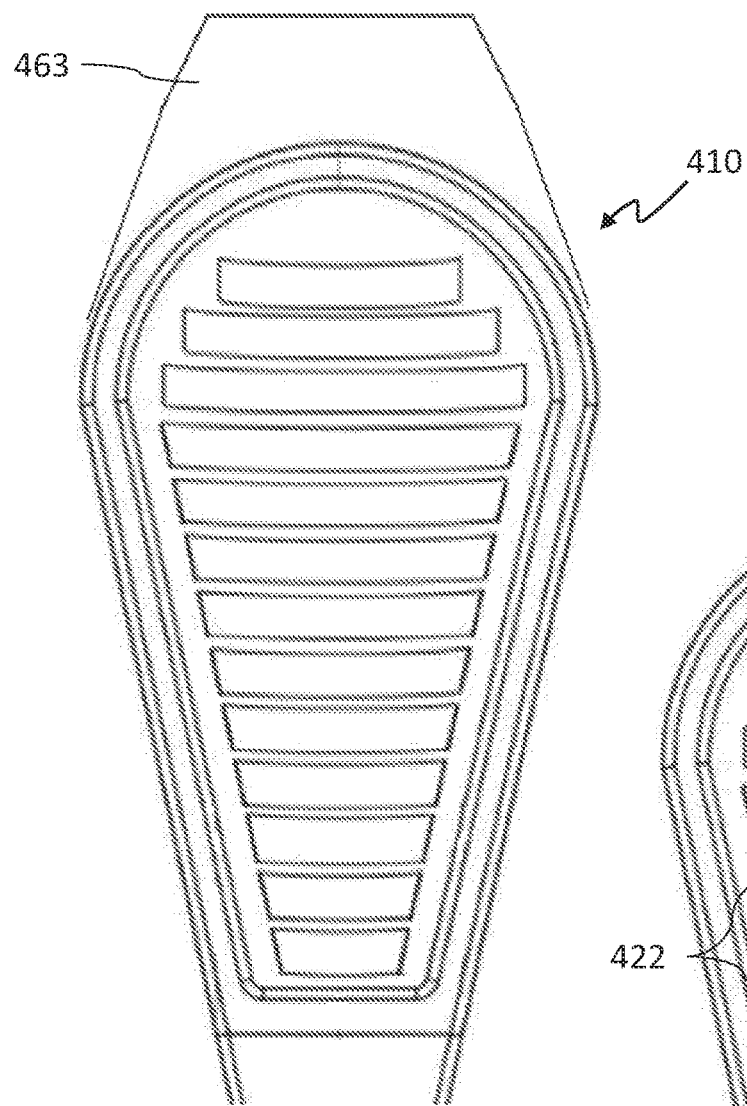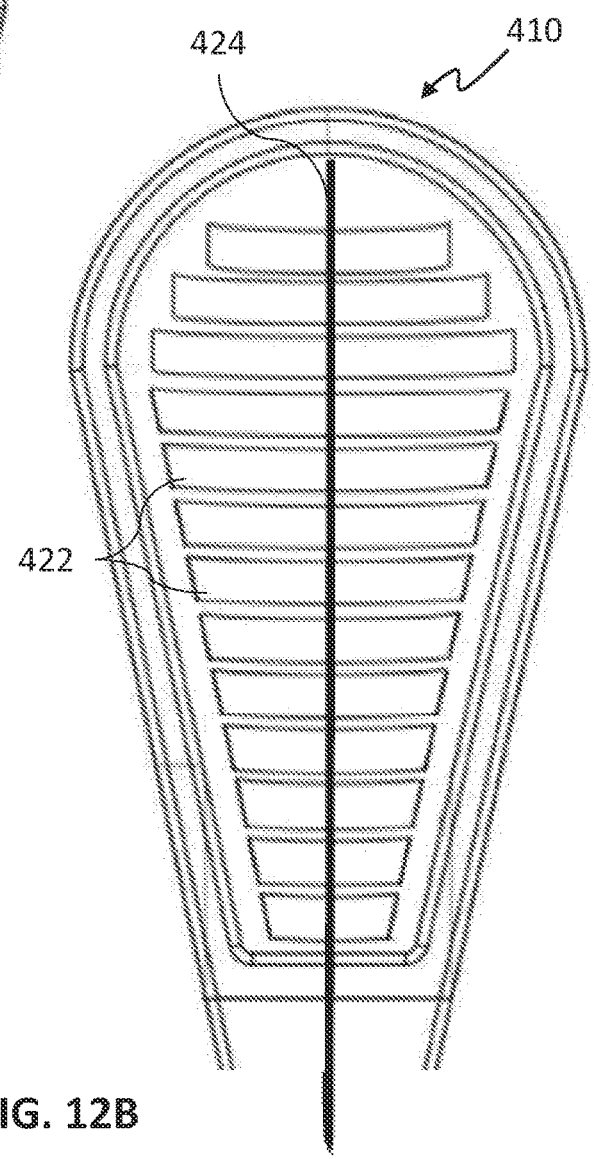
FIG. 12A
FIG. 12B

FIG. 14A
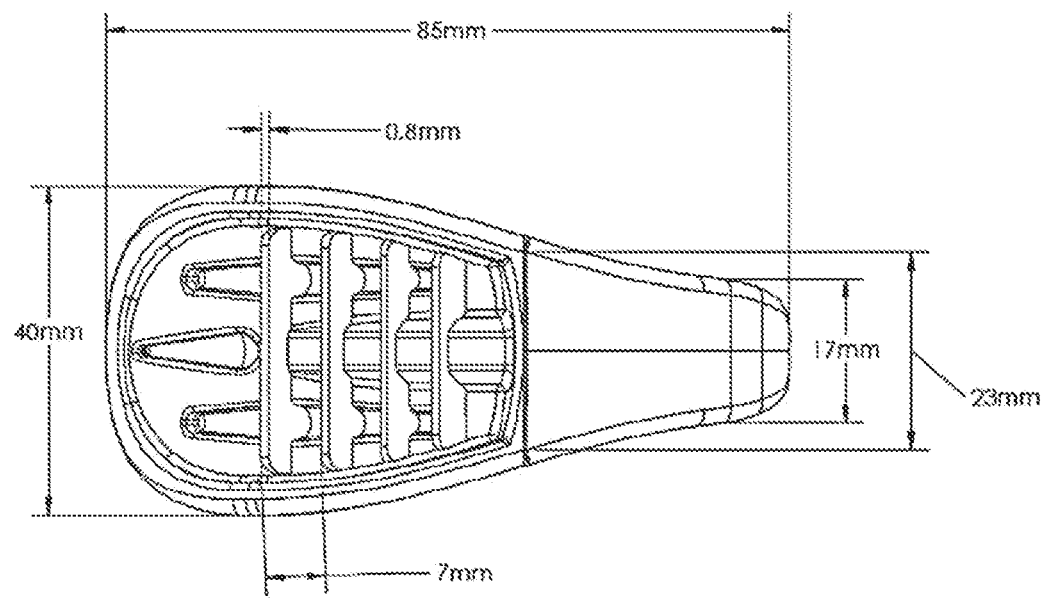
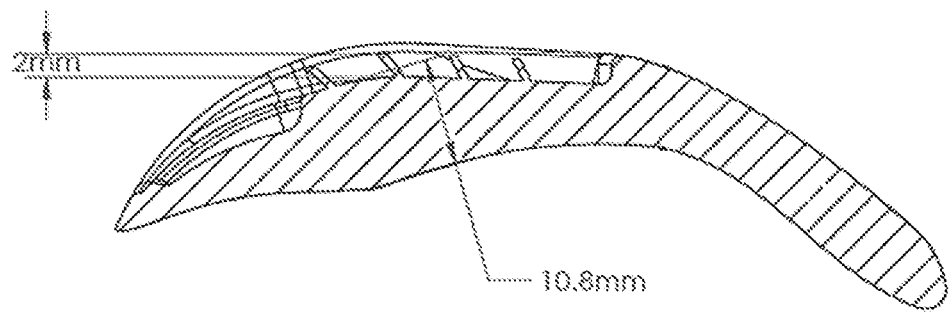
FIG. 14B

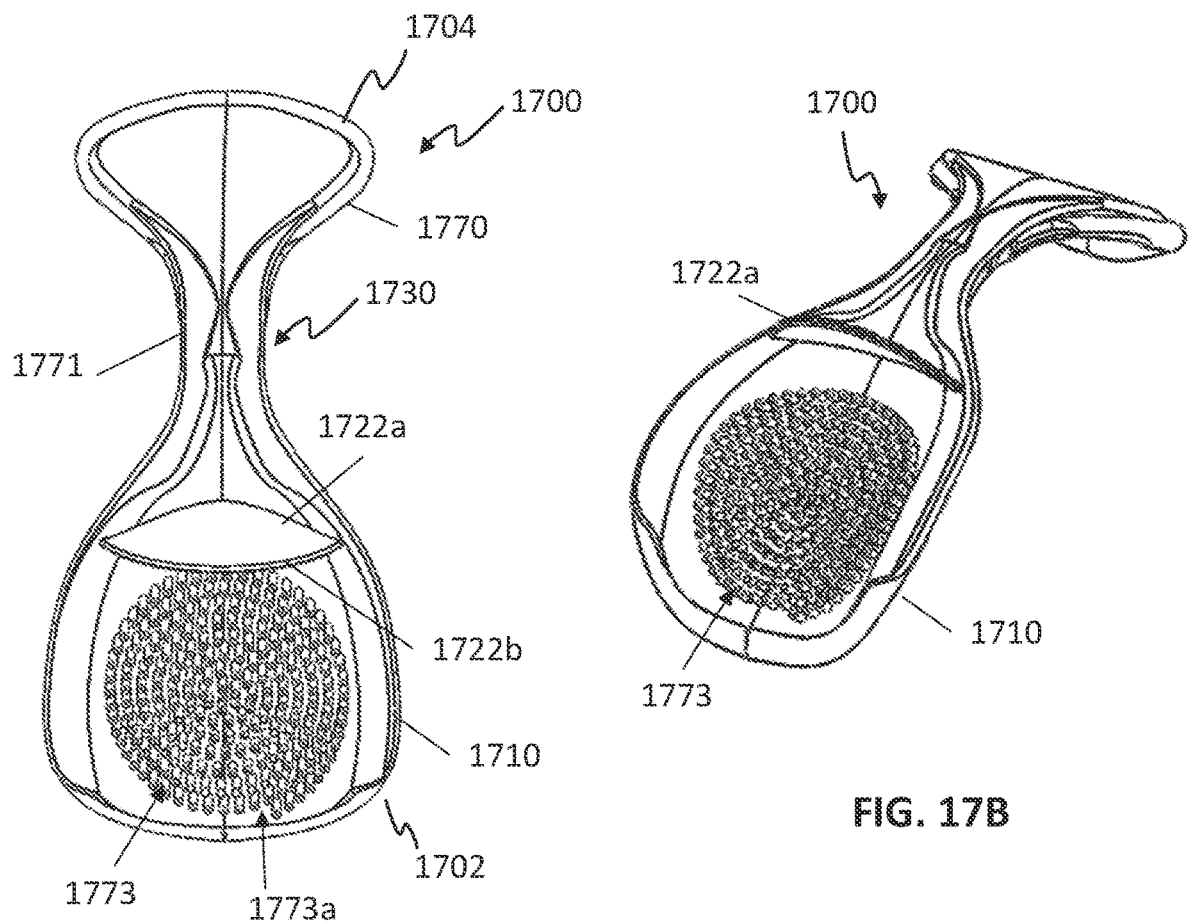
FIG. 17A
FIG. 17B
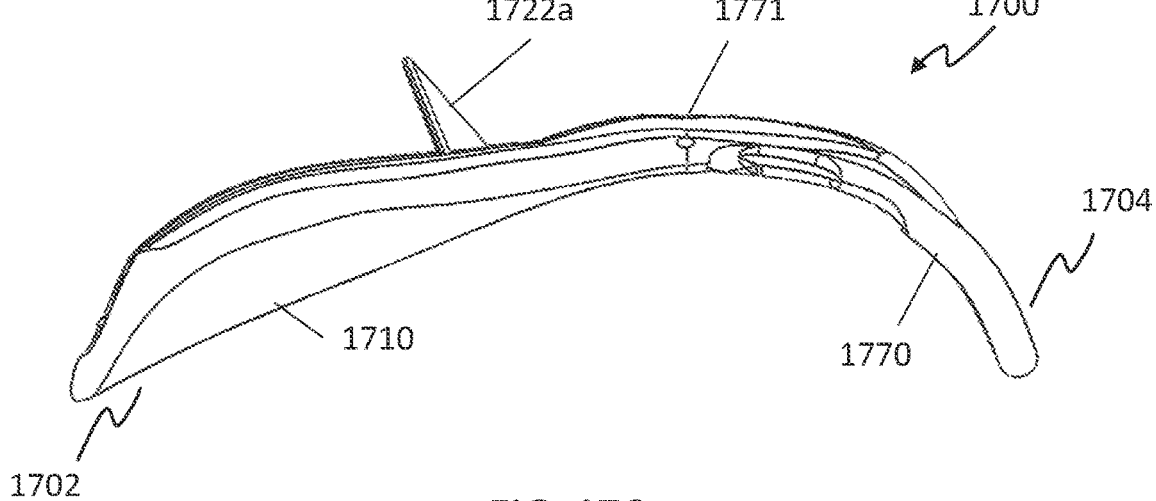
FIG. 17C

DEVICES AND METHODS FOR AIDING CONCEPTION

CROSS-REFERENCE TO RELATED APPLICATIONS

This application is a continuation of U.S. patent application Ser. No. 17/025,680 filed Sep. 18, 2020, issued as U.S. Pat. No. 11,357,481 on Jun. 14, 2022, which claims priority to U.S. Provisional Patent Application No. 63/017,291 filed Apr. 29, 2020, and U.S. Provisional Patent Application No. 62/902,491 filed Sep. 19, 2019, each of which is incorporated herein in its entirety by reference.

TECHNICAL FIELD

This invention relates generally to the field of devices and methods for assisting reproduction, and such as for aiding conception.

BACKGROUND

Infertility, which is clinically defined as an inability to conceive a child within twelve month despite attempts, is a common condition. For example, infertility affects as many as one in six couples trying to conceive. While causes of infertility may vary, nearly 60% of infertility is attributable to low sperm count or motility, or is unexplained infertility with unknown causes.

Conventional treatments for infertility include medications such as those to assist with hormone balance and/or ovulation. Assisted reproductive techniques may also help with conception. For example, intrauterine insemination (IUI) involves the artificial placement of externally-collected sperm into the uterus. As another example, in vitro fertilization (IVF) involves harvesting multiple eggs matured through a several months'-long course of fertility drugs, externally combining the mature eggs with sperm to form embryos, and introducing the embryos into the uterus.

However, these conventional treatments are not only invasive and often accompanied by undesirable side effects, but also may be prohibitively expensive for those seeking infertility treatment. Additionally, even for those who do have access for the more expensive treatments, procedures like IVF may only be performed a limited number of times per year, which impacts both success rate and family planning. Furthermore, many of these conventional treatments are clinic-based, which negatively impacts intimacy between partners. Accordingly, there is a need for new and improved devices and methods for providing people with a safe, easy, and affordable treatment that can be used on a frequent basis to increase their overall likelihood of a successful pregnancy.

SUMMARY

Generally, in some variations, a conception aid device (also referred to herein as a "conception aid device" or a "conception aid") may include a platform configured for placement in a vaginal canal, where the platform may include one or more capturing elements configured to collect semen. The platform may have any shape and/or size for insertion and placement in a vaginal canal. For example, in some variations the platform may include at least one preformed curve along a longitudinal axis between a proximal portion and a distal portion of the platform. Additionally or alternatively, the platform may have a width tapering along a longitudinal axis between a proximal portion and a distal portion of the platform. In some variations, the platform and/or other portions of the conception aid device may include a flexible material such as silicone. In some variations, the conception aid device may include a frame, spine, etc. to help provide structural support to the platform and/or other portion of the conception aid.

The one or more capturing elements may include one or more features suitable for collecting semen. For example, in some variations the one or more capturing elements may include one or more ridges (e.g., blades, flaps, fins, etc.) configured to trap and collect semen. The ridges may, for example, be arranged laterally across the platform and/or angled. As another example, the one or more capturing elements may additionally or alternatively include one or more recesses (e.g., wells), channels (e.g., longitudinal channels), pockets, and/or the like configured to trap and collect semen. As another example, the one or more capturing elements may additionally or alternatively include one or more filaments configured to trap and collect semen. The filaments may, for example, include single filaments arranged in an array (e.g., hair-like) and/or woven filaments (e.g., mesh). In some variations, the one or more capturing elements may include one or more through-holes within the conception aid, wherein the through holes are configured to allow passage of sperm therethrough. The one or more through-holes may, for example, allow for sperm that are trapped underneath the conception aid during intercourse to travel to a proximal end of the conception aid, (e.g., where the remaining capturing elements are positioned), and thus be aided towards the cervix.

In some variations, the conception aid may include an extending member coupled to and extending from the platform. In some variations, the extending member may be angled relative to the platform. For example, the extending member may be coupled to a distal portion of the platform. The extending member may, for example, extend distally from the platform such that the extending member may be manually grasped for guiding insertion of the platform into the vaginal canal and/or the extending member may help guide movement of a penis over the platform (and/or other portion of the conception aid) during intercourse. In some variations, the extending may be separately formed and coupled to the platform, or may be integrally formed with the platform.

In some variations, the conception aid may be configured to engage with a depositing device (e.g., syringe). For example, the conception aid may include a lumen (e.g., in the extending member) that is configured to receive a depositing device that introduces semen to the conception aid, such as to one or more capturing elements (e.g., pocket). As another example, the conception aid may be shaped to receive a depositing device over the platform, such that the depositing device introduces semen in a manner similar to delivery of semen through ejaculation during intercourse. In some variations, the lumen may include one or more valves (e.g., self-sealing valve). The lumen may have varying diameter (e.g., narrowing in diameter along a distal direction or proximal direction). Furthermore, in some variations the extending member may include a stop guide configured to guide insertion of the depositing device within the lumen, such as to help indicate or control depth of insertion of the depositing device relative to the conception aid.

Generally, in some variations, a method of aiding conception may include providing a conception aid device including one or more capturing elements, collecting semen with the one or more capturing elements, where the one or more capturing elements is configured to contain the collected semen on the conception aid device, and positioning the conception aid device in a vaginal canal. In some variations, collecting semen may be performed before positioning the conception aid device in the vaginal canal (e.g., semen may be collected when the conception aid device is external to the vaginal canal). Additionally or alternatively, collecting semen may be performed after positioning the conception aid in the vaginal canal (e.g., semen may be collected prior or during intercourse).

In some variations, the conception aid device may be positioned such that at least a portion of the one or more capturing elements is proximate a cervix. For example, a first portion of the conception aid device may be proximate a posterior fornix and a second portion of the conception aid device may be against a vaginal wall. In some variations, the conception aid device may collect semen while in a different position, before being moved to the above-described position with a portion proximate a posterior fornix and a portion against a vaginal wall.

Furthermore, in some variations, collection of semen may be performed with the use of a depositing device (e.g., syringe). The depositing device may, for example, be introduced over the conception aid device in introduce semen into the conception aid device. Additionally or alternatively, the depositing device may be introduced into a lumen of the conception aid device.

Generally, in some variations, a method of aiding conception may include positioning a device at a first position in a vaginal canal where the device includes one or more capturing elements, collecting semen with the one or more capturing elements (e.g., after positioning the device at the first position), and positioning the device at a second position in the vaginal canal such that at least a portion of the one or more capturing elements is proximate a cervix. For example, the device may be positioned at the first position prior to or during intercourse (e.g., at a location suitable for collecting semen), and the device may be positioned at the second position after intercourse (e.g., at a location suitable for positioning collected semen proximate or against the cervix). In some variations, the device may include, for example, a platform including the one or more capturing elements, and an extending member coupled to a distal portion of the platform.

For example, in some variations positioning a device at the first position in the vaginal canal may include positioning at least a portion of the device against a vaginal wall. In variations in which the device includes a platform and an extending member coupled to a distal portion of the platform, positioning the device at the first position in the vaginal canal may include positioning the extending member proximate the entrance of the vaginal canal. Additionally, in some variations a distal portion of the extending member may be positioned outside of the entrance of the vaginal canal.

Furthermore, in some variations, positioning the device at a second position in the vaginal canal may include positioning a first portion of the device in a posterior fornix and positioning a second portion of the device against the vaginal wall. For example, when the device is in the second position, a portion of the platform with the collected semen may be positioned proximate the cervix.

In some variations, the method may further include maintaining the platform at the second position in vaginal canal for a period of time, such as up to one hour, two hours, three hours, four hours, five hours, six hours, or more (e.g., following completion of intercourse).

BRIEF DESCRIPTION OF THE DRAWINGS

FIGS. 1A-1F depict schematic illustrations of an exemplary variation of a conception aid.

FIGS. 12A-12D depict top plan views of a variation of a conception aid platform and further variations of sperm capturing features within the platform.

FIGS. 14A-14B and 15A-15C depict schematic illustrations of variations of a conception aid having exemplary dimensions.

FIGS. 17A-17C depict schematic illustrations of another exemplary variation of a conception aid.

DETAILED DESCRIPTION

Figure 1A:
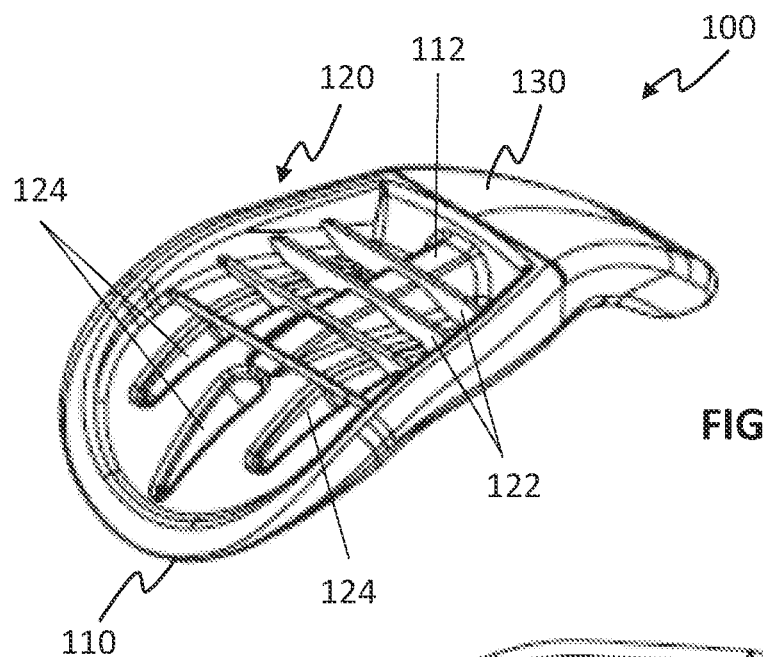

Non-limiting examples of various aspects and variations of the invention are described herein and illustrated in the accompanying drawings.

Described herein are variations of devices and methods for aiding conception. For example, a device may be temporarily implanted within the vaginal canal of a female intending to conceive. Generally, in some variations, a conception aid device may include a platform configured for placement in a vaginal canal, where the platform may include one or more capturing elements configured to collect semen.

The conception aid may be used during intercourse and work by trapping and guiding sperm towards the cervix. The conception aids may prevent the flowback of sperm, or the loss of sperm from the vaginal tract after intercourse. By preventing flowback, the conception aid may help to deliver a higher number of sperm to the cervix than when the conception aid is not used during intercourse. The conception aid may act as a sperm reservoir and can be left in the vaginal tract for a suitable period of time following intercourse, such as up to about one, two, three, four, five, six, seven, or more hours after intercourse.

Described herein are exemplary variations of such a conception aid. For example, in some variations a conception aid may include a platform conception aid including a platform configured for placement in a vaginal canal, where the platform may include one or more capturing elements configured to collect semen. The device may be positioned in the vaginal canal in a first position prior to or during intercourse (e.g., at a location suitable for collecting semen), and the device may be positioned at a second position such that at least a portion of the one or more capturing elements is proximate a cervix after intercourse (e.g., at a location suitable for positioning collected semen proximate or against the cervix). In some variations, the device may be positioned in the vaginal canal and receive a volume of semen before and/or after being positioned in the vaginal canal. For example, the semen may be received during intercourse or independent of intercourse (e.g., with a depositing device such as a syringe). Methods of using a platform conception aid are also further described herein.

As another example, in some variations a funneling conception aid may include an insertion member to be inserted into the vaginal canal and further includes a receptacle member to receive a penis during sexual intercourse. The insertion member may include a proximal opening positionable into proximity to a cervical opening, and the receptacle member may include a distal opening positionable into proximity to a vaginal opening. The insertion member and receptacle member may be in fluid communication with one another. Furthermore, at least one capturing member may be positioned between the proximal opening and distal opening such that the capturing member is configured to retain semen. The capturing member may extend proximally such that the capturing member is positionable into proximity to the cervical opening. Methods of using a funneling conception aid are also further described herein.

Platform Conception Aids and Methods of Use

Figure 1B:
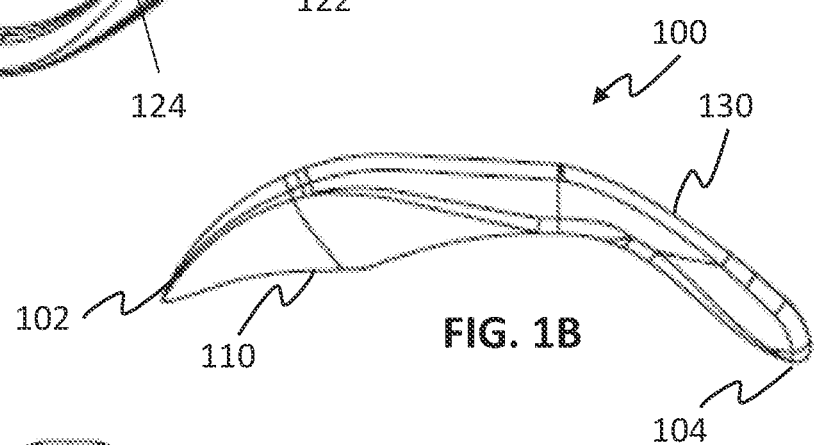
Figure 1C:
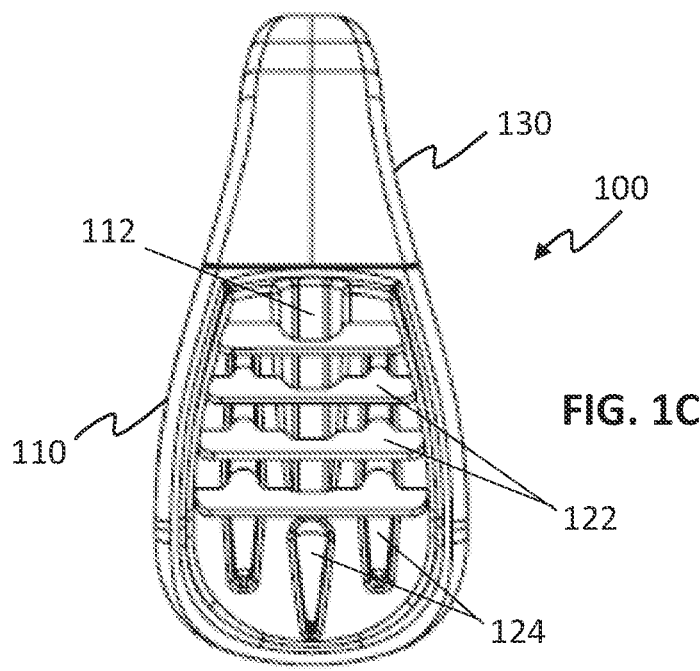

FIGS. 1A-1F depict schematic illustrations of an exemplary variation of a conception aid 100. FIGS. 1A-1C depict a top perspective view, a side view, and a top plan view, respectively, of the conception aid 100. FIGS. 1D-1F depict a view of the proximal end, a bottom plan view, and a bottom perspective view, respectively, of the conception aid 100.

The body of the conception aid 100 may include a platform 110 at a proximal end 102 of the device and an extending member 130 at a distal end 104 of the device. The extending member 130 may be coupled to the distal end 104. In some variations, the extending member may be integrally formed with the distal portion of the platform 110. Within the platform 110, capturing elements 120 may form a collection region of the conception aid 100 that can pool semen and/or prevent semen flowback. The capturing elements 120 can include features such as lateral ridges 122 and/or channels 124. The channels 124 may be longitudinal channels, and the conception aid may include one or more longitudinal channels 124. Other variations of capturing elements 120 are described in further detail below.

As is shown in FIG. 1B, the platform and/or overall body of the conception aid 100 may include at least one preformed curve along a longitudinal axis between a proximal portion of the platform 110, and a distal portion of the platform 110. For example, the platform of the conception aid 100 may formed such that when the conception aid 100 is in an unstressed or natural state, the conception aid 100 may be generally arched, with the proximal end 102 and the distal end 104 of the platform (or the extending member 130) curving away from the capturing elements 120. In some variations, the platform and/or overall body of the conception aid 100 may additionally or alternatively include at least one preformed curve along another axis (e.g., lateral to the longitudinal axis). Another example of a preformed curve can be seen in FIG. 18C, which depicts an exemplary conception aid 1800 having a platform 1810, wherein the platform comprises a U-shaped cross-section lateral to the longitudinal axis. The one or more preformed curves may, for example, help urge the capturing elements more closely against the cervix when the conception aid is positioned proximate the cervix after semen collection (e.g., as further described below), thereby improving likelihood of collected sperm entering the cervix. Additionally or alternatively, the one or more preformed curves may enable the device to engage against walls of the vaginal canal similar to a check valve, as described below with respect to FIG. 3B. Additionally or alternatively, the one or more preformed curves (e.g., along a lateral axis of the conception aid) may provide clearance to help avoid displacement of the conception aid during intercourse. In some variations, the platform and/or overall body of the conception aid 100 may have a preformed curve of a single radius of curvature, while in some variations the preformed curve may include various segments of different radii of curvature. In some variations, the radius of curvature is between about 5 mm to about 100 mm.

Additionally or alternatively, the preformed curve may be characterized as an angle between the extending member 130 and the general longitudinal axis of the platform 110. For example, an angle between the extending member 130 and the platform 110 may be between about 120 degrees and about 175 degrees, between about 120 degrees and about 160 degrees, between about 120 degrees about 150 degrees, between about 135 degrees and about 175 degrees, between about 135 degrees and about 160 degrees, between about 135 degrees and about 150 degrees, or between about 150 degrees and about 175 degrees.

In some variations, the thickness of the platform may be configured to provide sufficient support and/or rigidity of the device along multiple directions (e.g., X, Y, and Z axes), and/or torsional rigidity. In some variations, thickness of the platform may vary along its length. For example, as shown in FIG. 1B, the proximal end 102 may include a tapered thickness which may, for example, help facilitate an easier insertion of the conception aid 100 into the vagina and/or an easier placement of the conception aid 100 under the cervix, and/or help prevent the penis from hitting the conception aid 100. The thickness of the platform may also be varied to control stiffness or flexibility of the device along its length. For example, the ratio between the thickest portion of the thinnest portion of the platform may be between about 1.1:1 to about 2:1, between about 1.1:1 to about 1.75:1, between about 1.1:1 to about 1.5:1, between about 1.1:1 to about 1.25:1, between about 1.25:1 to about 2:1, between about 1.25:1 to about 1.75:1, between about 1.25:1 to about 1.5:1, between about 1.5:1 to about 2:1, between about 1.5:1 to about 1.75:1, or between about 1.1:1 to about 10:1. In some variations, thin regions of the conception aid may enable bending of the conception aid. Bending of the conception aid may, for example, allow for easier insertion and removal of the conception aid.

Additionally/or alternatively, in some variations, the width of the platform may vary along a longitudinal axis between a proximal portion and a distal portion of the platform. For example, as shown in FIGS. 1A and 1E, the proximal end 102 of the conception aid 100 comprising the platform 110 may be wider than the distal end 104 comprising the extending member 130. The shape formed by the platform 110 being wider than the extending member 130 may, for example, provide greater surface area for collecting semen with one or more capturing elements and/or may help to prevent the conception aid 100 from slipping out of the vaginal tract during intercourse. For example, the ratio of the widest width of the platform to the width of the extending member may be between about 1.1:1 to about 5:1, or between about 1.1:1 to about 2:1.

In some variations, the conception aid 100 may further include a spine 112 extending along at least a portion of the length of the platform 110, where the spine 112 may, for example, provide additional structural support to the conception aid 100. The spine 112 may extend along at least a portion of the platform 110, such as at about 25%, about 50%, about 75%, about 85%, about 90%, or the entirety of the length of the platform 110. For example, the spine 112 may extend generally in a longitudinal direction between the proximal end 102 and the distal end 104 of the platform 110. As another example, the spine 112 may be angled relative to a longitudinal axis extending between the proximal end 102 and the distal end 104 of the platform 110. In some variations, the conception aid 100 may include multiple spines, such as two, three, four, five, or more spines. In variations of the conception aid 100 including multiple spines, at least some of the spines may be longitudinally arranged in parallel, and/or at least some of the spines may be angled (e.g., fanned). In some variations, the one or more spines 112 may additionally or alternatively extend into the extending member 130. The thickness of the spine 112 may furthermore vary along its length. For example, as shown in FIG. 1A, spine 112 may be thicker at its distal end (closer to device distal end 104) and taper in thickness toward its proximal end (closer to device proximal end 102). Such tapering may be linear or curvilinear.

The conception aid 100 may include one or more capturing elements 120. The one or more capturing elements may, for example, include one or more channels 124 and/or lateral ridges 122 configured to act as sperm trapping or pooling features.

The conception aid 100 may include one or more channels 124. At least one channel 124 may be included in the platform 110, in the extending member 130, or both the platform 110 and the extending member 130. At least a portion of the one or more channels 124 may generally extend longitudinally between proximal and distal ends of the conception aid 100. Each channel may be distinct, or at least some channels may converge together (e.g., at their proximal ends, or at their distal ends). At least a portion of the channels 124 may individually be narrower at the proximal end 110 of the conception aid for funnel and guiding sperm, and at least a portion of the channels 124 may be wider at the distal end 104 for pooling semen. As another example, at least a portion of the channels 124 may converge at the distal end 104 to create a wider recessed area in which semen can be collected and pooled. In some variations, such as in the example depicted in FIGS. 1A and 1C, the conception aid 100 may include at least one channel 124 that extends along nearly the entire length of the platform 110 or overall length of the conception aid 100 (e.g., about 75%, about 80%, about 85%, about 90%, or about 95% or more of the length of the platform 110 or conception aid 100). In some variations, some channels extend between the proximal end and distal end of the platform 110. In some variations, some channels do not extend to the proximal end of the platform 110, and/or to the distal end of the platform 110. In some variations, at least one channel 124 is aligned with the spine 112.

In some variations, at least a portion of the channels 124 may have varying depth, such that the conception aid includes various shallower and deeper areas within which semen can be trapped and collected. The channels 124 may curve along the curvature of the platform 110, as is best seen in FIG. 1A, for example, which may facilitating the guiding of sperm towards the proximal end 102 of the conception aid. In some variations, at least a portion of the channels 124 may have a rounded shape along the recessed bottom side. It should be understood that the recessed bottom side of a channel 124 can also be rectangular, circular, oval, or any other suitable shape. Additionally, while in some variations the conception aid may include three channels as shown in FIGS. 1A and 1C, it should be understood that the conception aids may include any other suitable number of channels 124, such as one, two, four, five, six, seven, eight, nine, ten, or at least ten channels 124. Furthermore, the channels may be generally arranged in a regular pattern (e.g., in a rectangular array or staggered array) such as spaced equidistant from one another, or may be arranged in irregularly spaced apart.

The conception aid 100 may include one or more lateral ridges 122. At least one lateral ridge 122 may be included in the platform 110, in the extending member 130, or both the platform 110 and the extending member 130. The one or more lateral ridges 122 may be arranged such that each lateral ridge 122 is tilted or angled towards the proximal end 102 of the conception aid. This may be useful, for example, in guiding semen towards to the proximal end 102 and/or pooling semen when the conception aid 100 is in use as further described below. The lateral ridges 122 may each be tilted at the same angle, or they may be tilted at varying angles. For example, relative to an upper surface of the platform, a lateral ridge 122 may be tilted between about 5 degrees and about 85 degrees (or 75 degrees, 65 degrees, 60 degrees, or 50 degrees), between about 15 degrees and about 85 degrees (or about 75 degrees, 65 degrees, 60 degrees, or about 50 degrees), or between about 20 degrees and about 85 degrees (or about 75 degrees, 65 degrees, 60 degrees, or about 50 degrees). Furthermore, although the lateral ridges 122 shown in the example of FIGS. 1A-1F are generally planar flaps, in other variations at least some of the lateral ridges 122 may be curved (e.g., scoop-like or concave), or include outwardly-extending contoured ridges.

The lateral ridges 122 may each have the same height, or at least a portion of the lateral ridges 122 may have varying heights. In some variations, the platform 110 may include a plurality of lateral ridges 122, wherein the ridges have varying heights, and thus create various shallower and deeper areas within which semen can be trapped and collected. In some variations, the lateral ridges 122 are parallel to each other. In some variations, the lateral ridges 122 are angled such that some ridges are not parallel. For example, a chevron pattern can be created by a plurality of angled lateral ridges 122, such that the chevron pattern may help collect and/or direct semen in a particular direction. The conception aid can include, for example, four lateral ridges 122, as shown as an example in FIGS. 1A and 1C. However, it should be understood that the conception aids disclosed herein can include any other suitable number of lateral ridges 122, such as one, two, three, five, six, seven, eight, nine, ten, or at least ten lateral ridges 122. It should also be understood that the lateral 122 can have a rectangular shape as shown in FIGS. 1A and 1C, or a curved blade shape, a triangular shape, an oval shape, or any other suitable shape.

It should be understood that the conception aids may include any of the capturing elements disclosed herein, or any combination of capturing elements disclosed herein. Furthermore, it should also be understood that the conception aids may additionally or alternatively include other suitable capturing elements described hereinafter, such as, for example, pockets, mesh, hair-like structures, and bumps.

FIG. 1D illustrates a front view of the platform 110. In some variations, the platform 110 can include a lateral concave shape, as shown in the front view of FIG. 1D. For example, the device may include a saddle shape. In some variations, the platform 110 may include a flexible material, such that the concave shape may allow for the conception aid 100 to partially curve or otherwise flex inwards to conform to the female anatomy when in use. Furthermore, one or more recesses such as the channels 124 may also help to facilitate the inward flexing of the device. Although the variation shown in FIG. 1D generally has a semi-circular concave shape with an arc length of about 180 degrees, it should be understood that other variations may include other suitable concave shapes. For example, in some variations the platform 110 may include a lateral concave shape having an arc length greater than 180 degrees (e.g., about 190 degrees, about 200 degrees, about 210 degrees, or more). As another example, in some variations the platform 110 may include a lateral concave shape having an arch length less than 180 degrees (e.g., about 170 degrees, about 160 degrees, about 150 degrees, or less). A greater arc length for the lateral concave shape may, for example, provide greater surface area and/or more capturing elements for increased capture of semen. On the other hand, a lesser arc length for the lateral concave shape may, for example, provide sufficient surface area and/or more capturing elements while providing more room for a penis to pass over the conception aid device. Furthermore, arc length and overall lateral concave shape may be sized and/or shaped for particular anatomy (e.g., smaller lateral concave shapes may be more suitable for use in narrower vaginal canals, and vice versa).

As best shown in FIG. 1B, the extending member 130 may be coupled to the platform 110 at the distal end 104. The extending member 130 coupled together with the platform 110 can provide stability and rigidity to the conception aid, in the three X, Y, Z axes of force. The extending member 130 may include a shaft, which can help facilitate the gripping and positioning of the conception aid by the user, and can include rounded edges at the distal end 104 to further facilitate gripping and to aid in the comfort of the user. Furthermore, the extending member 130 can be tapered or flared at the distal end, or include textured elements or ridges, or other frictional features, to aid the user in gripping the conception aid. In some variations, the extending member is smooth. The extending member 130 can be straight, or can include a curvature along the longitudinal axis of the conception aid. The general shape of the extending member 130 can also act as a guide for the penis during intercourse, such that the penis does not become obstructed by the platform 110 during intercourse (e.g., the extending member may act as a guide that helps prevent the penis from accidentally going under the device during intercourse). In some variations, the extending member can include a circular or elliptical cross-section. In some variations, the extending member has a varying width and/or diameter along the longitudinal axis of the conception aid. In some variations, the extending member maintains the same width and/or diameter along the longitudinal axis of the conception aid. In some variations, the length of the extending member can be adjusted by the user, such as by the addition or removal of another element. For example, a stopper element can be included on the extending member, as further discussed below when referring to FIG. 13.

In some variations, the conception aid may have a length that helps to position the conception aid proximate a cervical opening (e.g., against, below, or otherwise close to the cervix) while also functioning to help prevent over-insertion. For example, in some variations the conception aid may have a length such that when the platform is placed within the vaginal canal, the proximal portion of the platform is positioned proximate a cervical opening and at least a portion of the extending member is external to the vaginal canal. In other words, the conception aid may be sufficiently long such that when the platform is positioned against or abutting tissue in the vaginal canal (e.g., proximate the cervical opening, such as against the cervix or in the posterior fornix, etc.), this helps prevent over-insertion of the conception aid in the vaginal canal while still maintaining a retrievable portion of the external member. Example dimensions of the conception aid are described in further detail below.

Figure 2A:
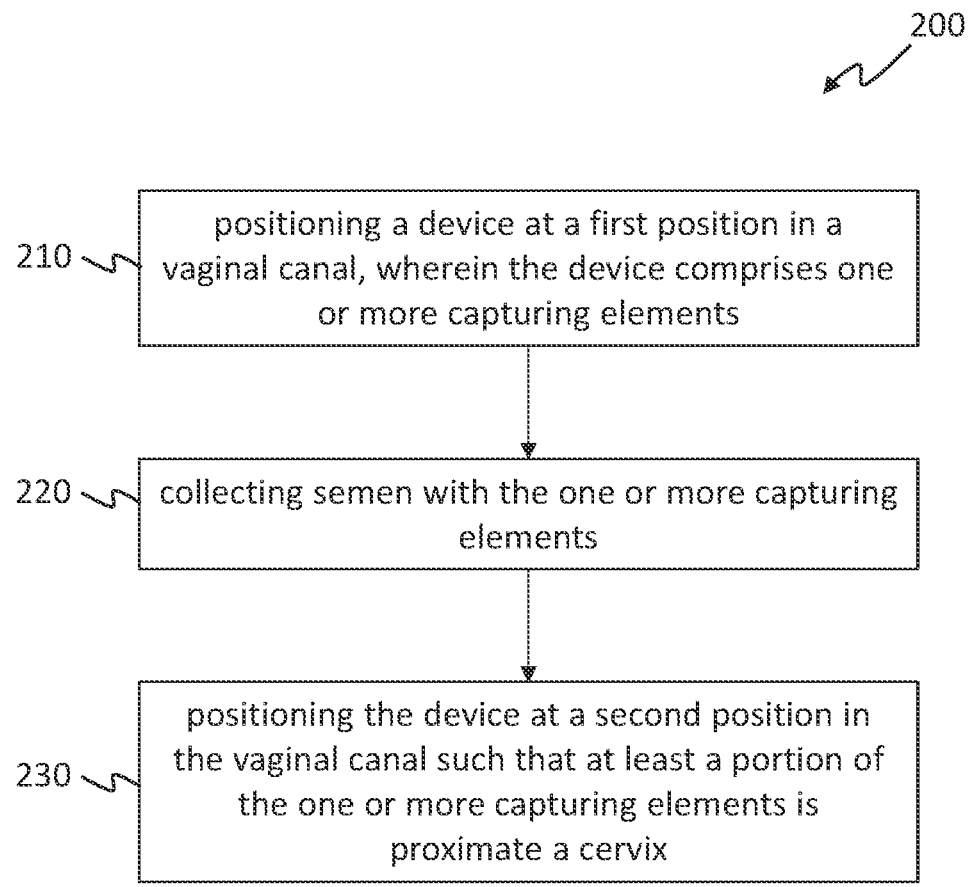
FIGS. 2A-2C are illustrative flowcharts of exemplary variations of a method for aiding conception.

FIG. 2A is an illustrative flowchart 200 of an exemplary variation of a method for aiding conception. As an example, the method depicted in FIG. 2A may be performed by using any variation of a conception aid disclosed herein. The method may include positioning a conception aid device at a first position in a vaginal canal, wherein the device includes one or more capturing elements (210). The one or more capturing elements may help to capture sperm and prevent semen flowback. The method may also include collecting semen with the one or more capturing elements (220). It should be understood that any of the capturing elements disclosed herein, or any combination of capturing elements disclosed herein, may be used for collecting semen. The method may also include positioning the device at a second position in the vaginal canal such that at least a portion of the one or more capturing elements is proximate a cervix (230). In some variations, positioning the device at the second position in the vaginal canal includes positioning the collected semen proximate the cervix. In some variations, the method further includes maintaining the platform at the second position in the vaginal canal for a period of time. For example, the conception aid may then be kept in the second position for about 6 hours.

Figure 2B:
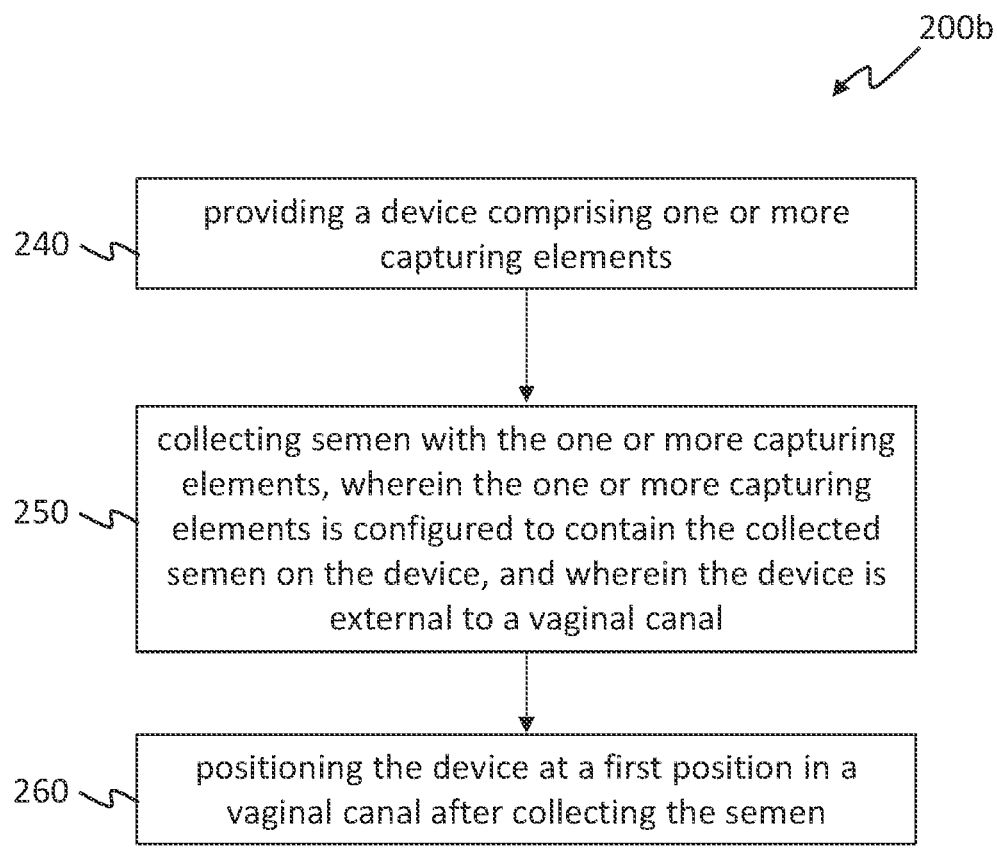

FIG. 2B is an illustrative flowchart 200b of another exemplary variation of a method for aiding conception. As an example, the method depicted in FIG. 2B may be performed by using any variation of a conception aid provided herein. The method may include providing a device comprising one or more capturing elements (240). The device may be any variation of a conception aid provided herein, and the one or more capturing elements may be any variation of the capturing elements provided herein. It should be understood that the conception aid used in the method depicted in FIG. 2B may include a combination of any of variations of the capturing elements provided herein. The method may also include collecting semen with the one or more capturing elements, wherein the one or more capturing elements is configured to contain the collected semen on the device, and wherein the device is external to a vaginal canal (250). For example, a device can be used externally such that ejaculated sperm can be collected and thereby contained on the device, wherein the capturing elements of the conception aid may facilitate protection of the sperm (such as protection from the relative acidic environment of the distal vaginal tract, for example). The method may also include positioning the device at a first position in a vaginal canal after collecting the semen (260). As an example, the capturing elements may also help to protect the sperm from spilling out or off of the device during movement or positioning of the device in step 260. The first position may place at least a portion of the capturing elements proximate a cervix, or the method may optionally include further positioning the device at a second position within the vaginal canal in order to place at least a portion of the capturing elements proximate a cervix.

Figure 2C:
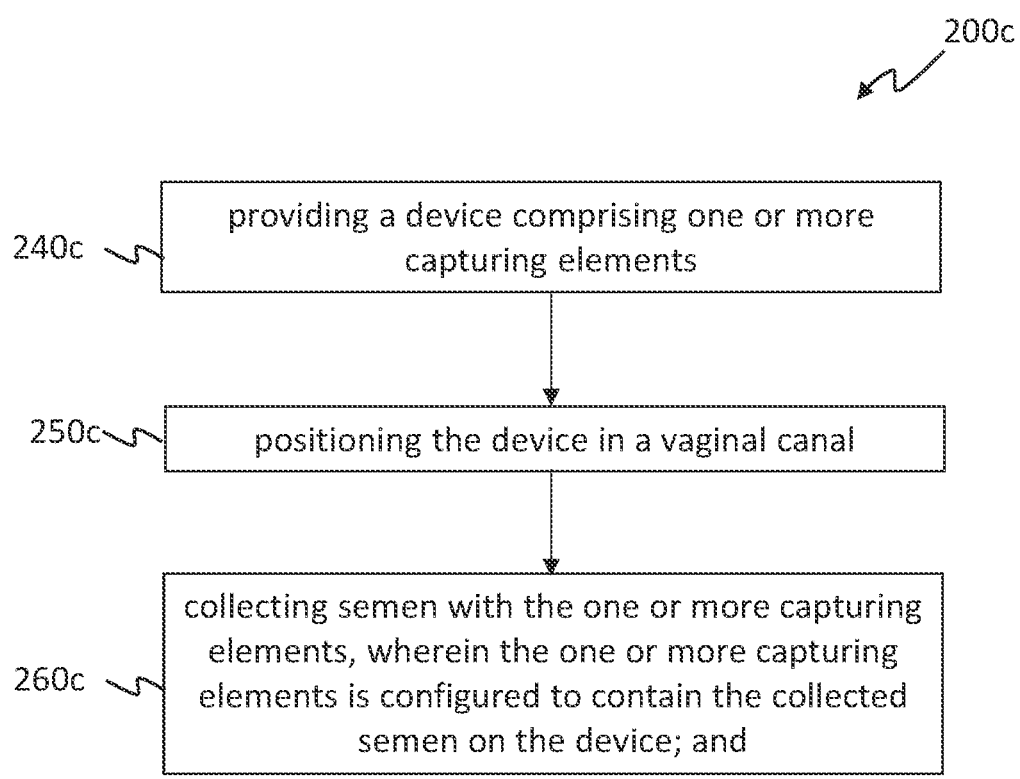

FIG. 2C is an illustrative flowchart 200c of another exemplary variation of a method for aiding conception. As an example, the method depicted in FIG. 2C may be performed by using any variation of a conception aid provided herein. The method may include providing a device comprising one or more capturing elements (240c). The device may be any variation of a conception aid provided herein, and the one or more capturing elements may be any variation of the capturing elements provided herein. It should be understood that the conception aid used in the method depicted in FIG. 2C may include a combination of any of variations of the capturing elements provided herein. The method may also include positioning the device in a vaginal canal (250c) such as proximate a cervix, and then collecting semen with the one or more capturing elements (260c), where the one or more capturing elements is configured to contain the collected semen on the device. As an example, the capturing elements may also help to protect the semen from spilling out or off of the device during movement or positioning of the device and/or may help direct semen toward the cervix. In some variations, semen may be collected onto the device internally during intercourse. Additionally or alternatively, semen may be obtained externally before, during, or after intercourse and then collected onto the device. In some variations, semen may be introduced for collection on the device via a depositing device (e.g., syringe) as further described below. The capturing elements of the conception aid may facilitate protection of the sperm (such as protection from the relative acidic environment of the distal vaginal tract, or protection from the external environment, for example). The method may also include positioning the device in a vaginal canal (260c). It should also be understood that step 260c can be performed before step 250c.

Any of the methods disclosed herein using any of the conception aids disclosed herein may also be performed with the use of a depositing device, for depositing semen or sperm onto the conception aid. The depositing device, which can be used with any of the conception aids disclosed herein, is discussed in further detail below.

Figure 3A:
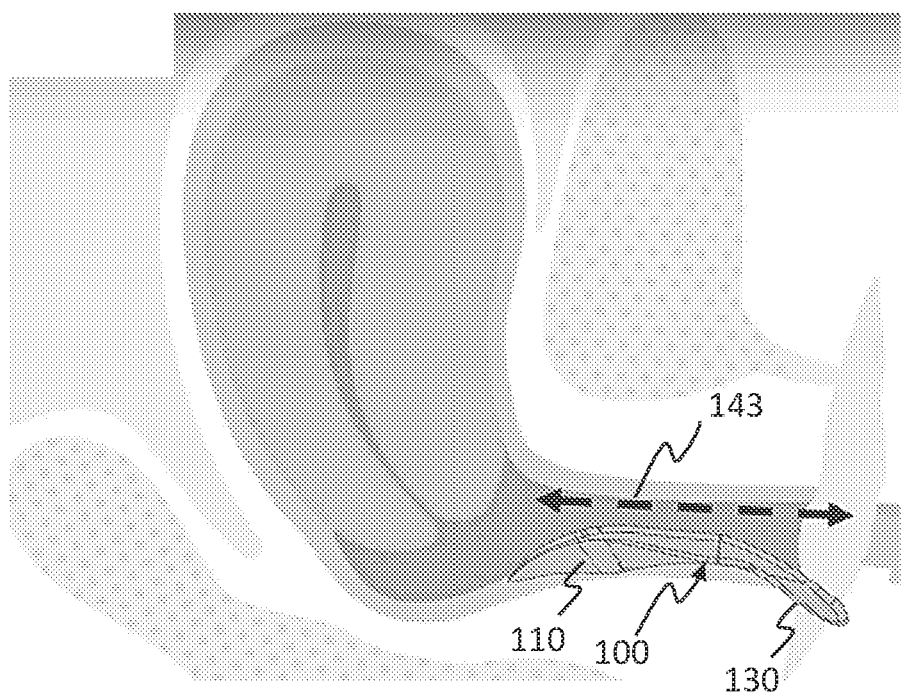
FIGS. 3A and 3B depict an exemplary variation of a method for aiding conception. As an example, the conception aid as shown in FIGS. 1A-IF may be used in the method for aiding conception.
Figure 3B:
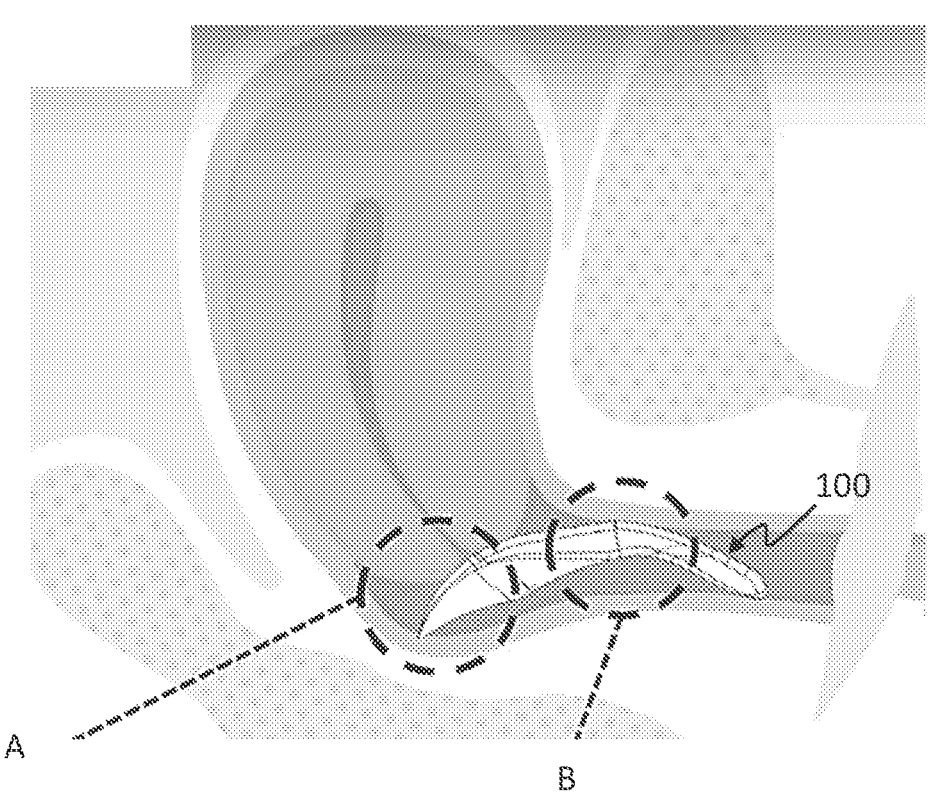

FIGS. 3A and 3B depict an exemplary variation of a method for aiding conception. As an example, the conception aid 100 described above (e.g. as shown in FIGS. 1A-1F) may be used in the method for aiding conception. FIG. 3A depicts an exemplary step in the method of aiding conception, similar to step 210 of the flow chart of FIG. 2. In other words, FIG. 3A depicts the conception aid 100 positioned at a first position in a vaginal canal. The capturing elements, as described when referring to FIGS. 1A-1F, may be included within the platform 110 for the capturing and pooling of semen. During intercourse, the penis can glide in the space above the conception aid, as shown by arrow 143, without being obstructed by any portion of the device. It should be understood that the conception aid 100 may be placed in a deeper or shallower position within the vaginal canal depending on the anatomy and comfort of the users. In some variations, positioning the device at the first position in the vaginal canal is performed prior to or during intercourse. In some variations, the method includes positioning the extending member proximate the entrance of the vaginal canal. In some variations, positioning the extending member proximate the entrance of the vaginal canal includes positioning at least a distal portion of the extending member outside of the entrance of the vaginal canal, as shown in FIG. 1A.

FIG. 3B depicts another exemplary step in the method of aiding conception, similar to step 230 of the flow chart of FIG. 2. In other words, FIG. 3B depicts the conception aid 100 positioned at a second position in a vaginal canal. In the second position in the vaginal canal, at least a portion of the one or more capturing elements within the platform 110 is proximate a cervix, or against a vaginal wall, shown in region A of FIG. 3B. In the second position, the platform 110 may sit directly under the cervix, with the proximal end of the conception aid being at the posterior fornix, again as shown in region A of FIG. 3B. In some variations, positioning the device at the second position in the vaginal canal includes positioning a first portion of the device in a posterior fornix and positioning a second portion of the device against the vaginal wall.

In some variations, the conception aid 100 may include a curvature such as one or more preformed curves as described above and as seen in the views of the device shown in FIGS. 3A-3B. The curvature may act as a "check valve," such that the conception aid 100 is pushed to a flat shape when in the first position as shown in FIG. 3A, when the penis is inside the vaginal canal during intercourse, and such that the conception aid 100 can return to a curved shape when the penis is withdrawn. The preformed curve or curved shape can further help to prevent semen flowback by remaining against a vaginal wall or the vaginal canal as shown in region B of FIG. 3B.

Figure 4A:
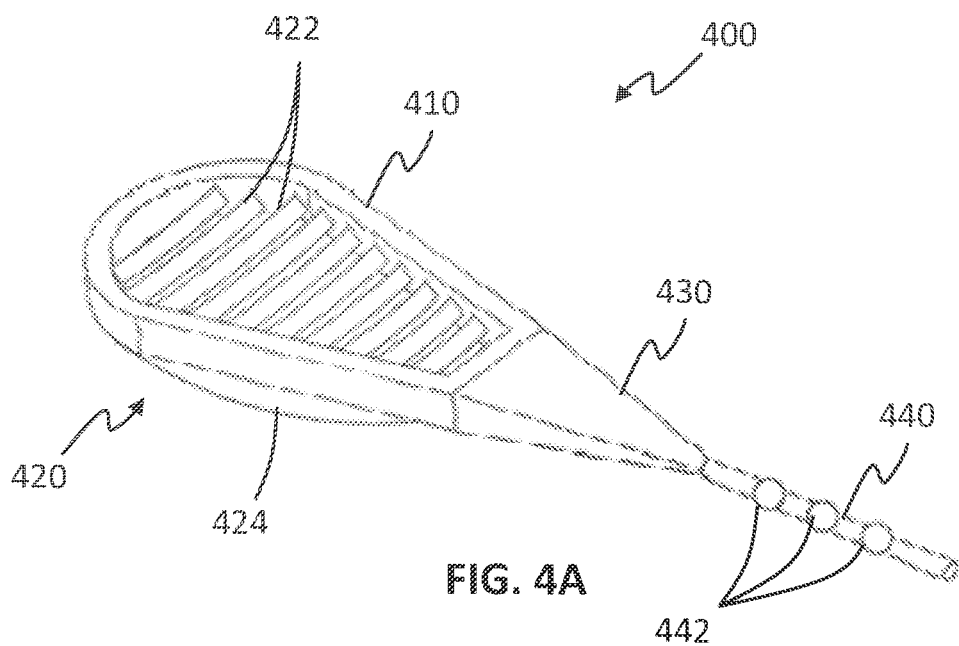
FIGS. 4A and 4B depict schematic illustrations of another exemplary variation of a conception aid.
Figure 4B:
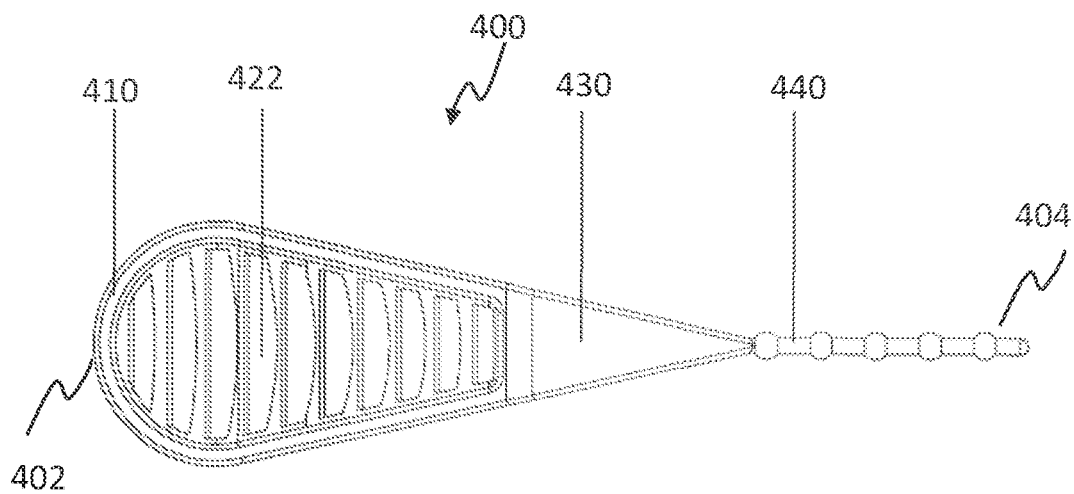

FIGS. 4A and 4B depict schematic illustrations of another exemplary variation of a conception aid 400. FIGS. 4A and 4B depict a top perspective view, and a top plan view, respectively, of the variation of a conception aid 400. Similar to the conception aid 100 depicted in FIGS. 1A-1F, the exemplary variation of a conception aid 400 may include a platform 410 at a proximal end 402 and an extending member 430 at a distal end 404. Accordingly, it should be understood that some variations of a conception aid may include any one or more features of the conception aid 400 as described herein combined with any one or more features of the conception aid 100 as described herein, in any suitable manner. Within the platform 410, one or more capturing elements 420 may form a collection region of the conception aid 400 that can pool semen and prevent semen flowback. The capturing elements 420 can include features such as lateral ridges 422 and channels 424. The extending member 430 may include a removal member 440 at the distal end 404, having textural elements 442 for ease of gripping the removal member 440 when removing the conception aid 400 from the vaginal canal. The textural elements 442 may protrude from the removal member 440, again, for ease of gripping onto the removal member 440.

The lateral ridges 422 may include a tilt, such that the lateral ridges 422 are tilted towards the proximal end 402. This tilted arrangement may help to trap semen within the collection region of the platform 410. Each of the lateral ridges may be positioned at the same angle towards the proximal end 402, or may be positioned at varying angles. Each of the lateral ridges may have the same height, or may have varying heights.

FIGS. 17A-17C depict schematic illustrations of another exemplary variation of a conception aid 1700. FIGS. 17A-17C depict a top plan view, a top perspective view, and a side view, respectively, of the variation of a conception aid 1700. Similar to the conception aid 100 depicted in FIGS. 1A-1F, the exemplary variation of a conception aid 1700 may include a platform 1710 at a proximal end 1702. The distal end 1704 may comprise an extending member, the extending member comprising an outer anchor 1770 and a neck 1771. The neck 1771 may be disposed between the platform 1710 and the outer anchor 1770, wherein the neck 1771 is narrower than both the platform 1710 and the outer anchor 1770.

In some variations, the platform 1770, the outer anchor 1770, and the neck 1771 may each have a width that is different from each other. Generally, the various portions of the conception aid 1770 may be provided with a curvature such that the width of the platform, the neck, and the outer anchor may vary, and may become smaller or larger along the longitudinal axis of the conception aid. In some variations, the width of the platform 1770 at the largest portion of the platform may be larger than the width of the outer anchor 1770 at the largest portion of the outer anchor, which may be larger than the width of the neck 1771 at the largest portion of the neck. In some variations, the width of the neck 1771 at the largest portion of the neck is approximately half, or one third, or one fourth of the width of the outer anchor 1770 at the largest portion of the outer anchor.

The outer anchor 1770 may include a generally flared, oval, circular, or ellipsoidal shape, and may help to prevent the conception aid 1700 from slipping out of a desired position within the vaginal canal during intercourse. In some variations, the extending member is angled relative to the platform 1770. As can be best seen in FIG. 17C, the outer anchor 1770 may be curved generally towards the bottom end of the conception aid 1700, which can further aid in anchoring the conception aid 1700 in a desired position when in use within the vaginal canal. Thus, the conception aid 1700 may be prevented from moving further into the vaginal canal until the user repositions the conception aid manually, for example. The outer anchor 1770 may also provide a means for the user to easily grip the conception aid 1700.

In some variations, a curvature is provided extending longitudinally between the outer anchor 1770 and the platform 1710 on the sides of the conception aid 1700, such that the conception aid 1700 may more comfortably fit and/or flex to accommodate a user's anatomy, and/or such that the conception aid 1700 can be further anchored in place by the outer anchor 1770. The curvature may also be combined with a narrowing of the conception aid between the outer anchor 1770 and the platform 1710, providing the narrowed shape of the neck 1771, which can also be referred to as a narrowed region of the extending member 1730. The narrowed neck 1771 may also provide more access space within the vagina, and thereby facilitate an easier penetration of the penis into the vagina during intercourse while the conception aid 1700 has been placed into the vaginal canal.

Figure 5A:
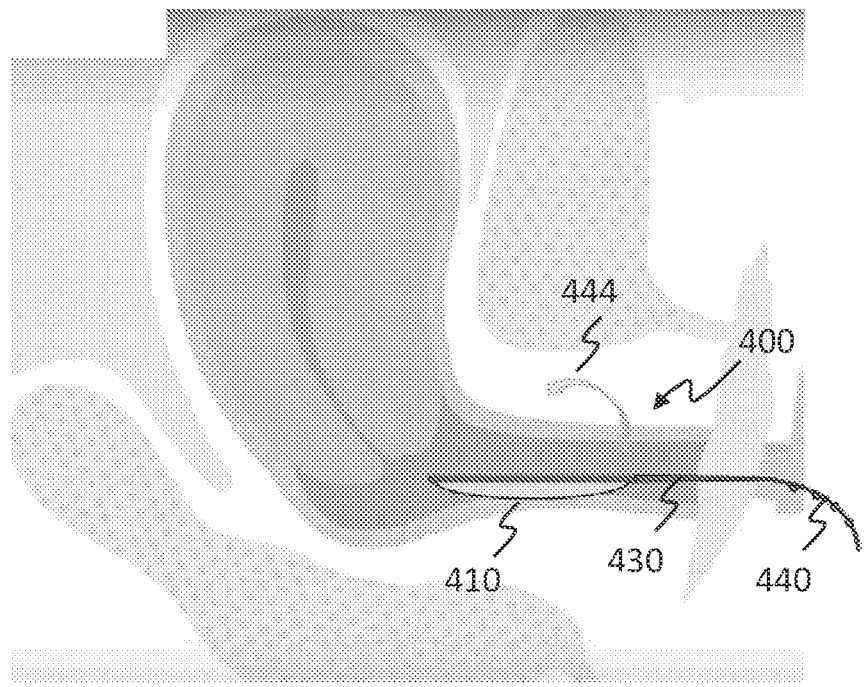
FIGS. 5A and 5B depict another exemplary variation of a method for aiding conception. As an example, the conception aid as shown in FIGS. 4A and 4B may be used in the method for aiding conception.
Figure 5B:
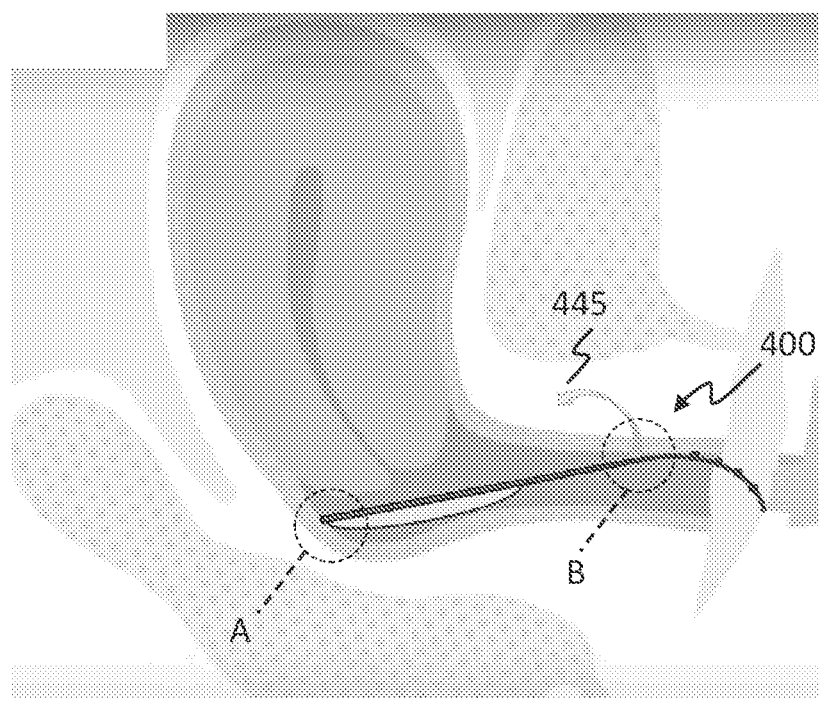

The conception aid 1700 may also be provided with another variation of a lateral ridge, which can be fin-shaped ("fin-shaped lateral ridge") 1722a, which may include a flat shape and a curved upper edge 1722b. Again, as described above, the platform 1710 may generally taper to provide a curvature to the sides of the conception aid 1700. The fin-shaped lateral ridge 1722a may be positioned at approximately the portion of the platform 1710 that begins to taper towards the neck 1771. The fin-shaped lateral ridge 1722a may be tilted towards the proximal end 1702, to facilitate the guiding of sperm towards the cervix. For example, relative to an upper surface of the platform, a fin-shaped lateral ridge 1722a may be tilted between about 5 degrees and about 85 degrees (or 75 degrees, 65 degrees, 60 degrees, or 50 degrees), between about 15 degrees and about 85 degrees (or about 75 degrees, 65 degrees, 60 degrees, or about 50 degrees), or between about 20 degrees and about 85 degrees (or about 75 degrees, 65 degrees, 60 degrees, or about 50 degrees). The fin-shaped lateral ridge 1722a may have a generally flat body shape, or may be curved such that the fin-shaped lateral ridge forms a cupping shape relative to the platform 1710. Furthermore, a top edge of the fin-shaped lateral ridge 1722a may be curved or arched so as to be atraumatic and/or conform to the vaginal wall of a user. FIGS. 5A and 5B depict another exemplary variation of a method for aiding conception. As an example, the conception aid as shown in FIGS. 4A and 4B may be used in the method for aiding conception. FIG. 5A depicts an exemplary step in the method of aiding conception, similar to step 210 of the flow chart of FIG. 2. In other words, FIG. 5A depicts the conception aid 400 positioned at a first position in a vaginal canal. In some variations, positioning the device at the first position in the vaginal canal is performed prior to or during intercourse. In some variations, the method includes positioning the extending member proximate the entrance of the vaginal canal. In some variations, positioning the extending member proximate the entrance of the vaginal canal includes positioning a distal portion of the extending member outside of the entrance of the vaginal canal. The capturing elements, as described when referring to FIGS. 4A and 4B, may be included within the platform 410 for the capturing and pooling of semen. As shown by arrow 444, the conception aid 400 may be placed downwards to allow a space above the device for the penis such that the penis is not obstructed by the device during intercourse.

FIG. 5B depicts another exemplary step in the method of aiding conception, similar to step 230 of the flow chart of FIG. 2. In other words, FIG. 5B depicts the conception aid 400 positioned at a second position in a vaginal canal. In the second position in the vaginal canal, at least a portion of the one or more capturing elements within the platform 410 is proximate a cervix, shown in region A of FIG. 5B. In the second position, the platform 510 may sit directly under the cervix, with the proximal end of the conception aid being at the posterior fornix, again as shown in region A of FIG. 5B. The second position of the conception aid 400 within the vaginal canal can be achieved by tilting the conception aid 400 in the upwards direction shown by arrow 445, and pushing the conception aid 400 further into the vaginal canal. In some variations, positioning the device at the second position in the vaginal canal includes positioning a first portion of the device in a posterior fornix and positioning a second portion of the device against the vaginal wall. A user may grasp the removal member 440 to change the position of the conception aid 400 within the vaginal canal.

In some variations, the removal member 440 may include a curvature, as shown in FIGS. 5A and 5B. In some variations, positioning the device at the second position in the vaginal canal includes positioning the collected semen proximate the cervix. In some variations, the method further includes maintaining the platform at the second position in the vaginal canal for a period of time. For example, the conception aid 400 may be kept in the second position within the vaginal canal at the cervix for about 6 hours.

Platform Conception Aid Variations

In some variations, a conception aid may additionally or alternatively include other various features as described below. Although these features are shown and described primarily with respect to a conception aid similar to that described above with respect to FIGS. 4A and 4B, it should be understood that these features may be included in a conception aid similar to that described above with respect to FIGS. 1A-1F.

Platform and Extending Member

FIGS. 6A-6D depict schematic illustrations of a top plan view, a front view, a side view, and a detailed top plan view of the platform 410 region, respectively, of a variation of a conception aid 400. Again, a conception aid 400 may include a platform 410, and an extending member 430, which can help the conception aid to maintain its shape and structure. Lateral ridges 422 may be included throughout the platform 410. As an example, a conception aid may include between about five and fifteen lateral ridges 422. The lateral ridges 422 may be tilted at an angle towards the proximal end of the conception aid 400. An exemplary angle of the lateral ridges is about 45°, or about 45° to about 90°. The height of the lateral ridges 422 above the base of the platform 410 may vary, for example, or each of the lateral ridges 422 may have the same height.

Figure 6A:
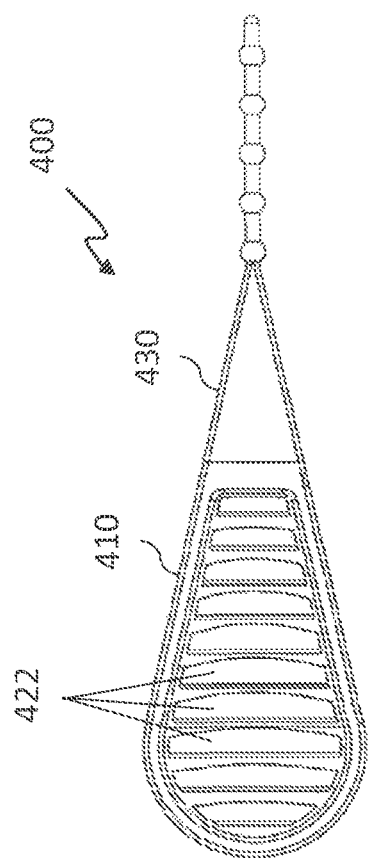
FIGS. 6A-6D depict schematic illustrations of a top plan view, a front view, a side view, and a detailed top plan view of a portion of the platform region, respectively, of an exemplary variation of a conception aid.
Figure 6C:
Figure 6B:
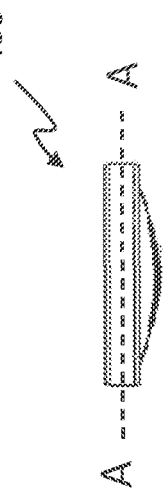

The axes depicted by line A-A of FIG. 6B and line B-B of FIG. 6C refer to regions of the conception aid 400 that may have a positive or negative curvature, for example. As another example, axes A-A and B-B may have a combination of different curvatures. An exemplary radius of curvature at axes A-A and B-B is between about 20.0 mm and about 50.0 mm.

Figure 6D:
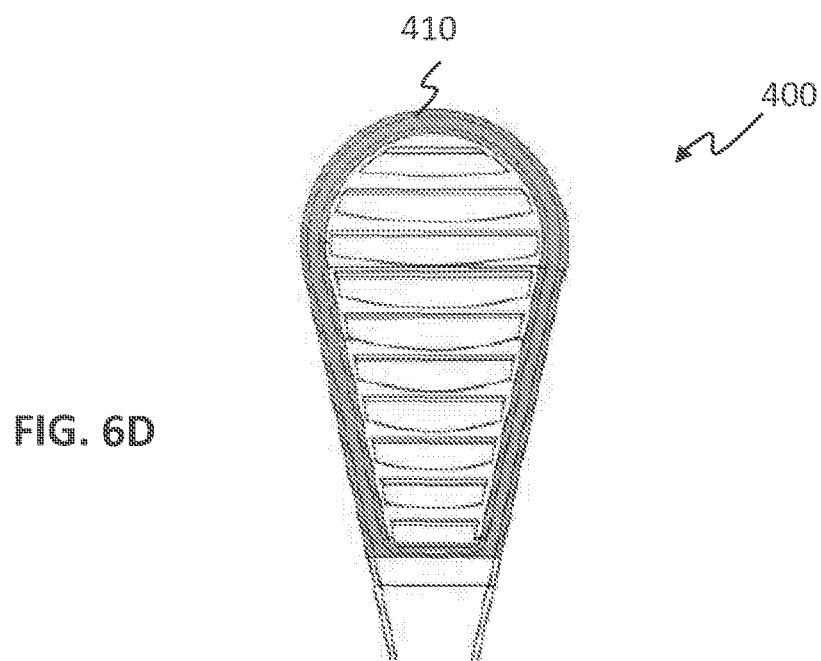

FIG. 6D depicts an exemplary shape of the platform 410 of a variation of a conception aid 400. In some variations, the shape of the platform 410 may be generally oval or teardrop-shaped as shown. In some variations, the platform 410 may be circular, oval, rectangular, square, or a combination of any suitable shapes. In some variations, the shape of the platform 410 may be discontinuous with a single or multiple openings. In some variations, the platform 410 may be recessed to include an interior surface, within which sperm can be collected and trapped.

Figure 7A:
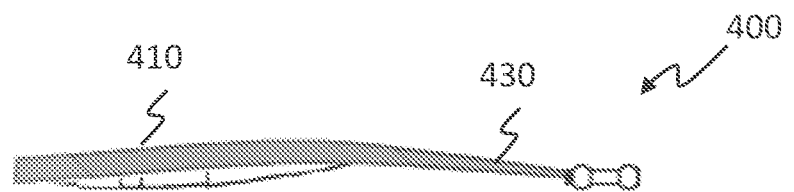
FIGS. 7A-7E depict different variations of the platform and extending member of a conception aid.
Figure 7B:
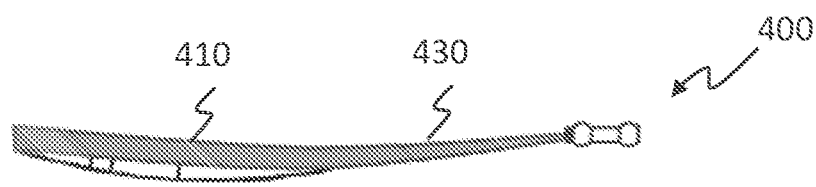
Figure 7C:
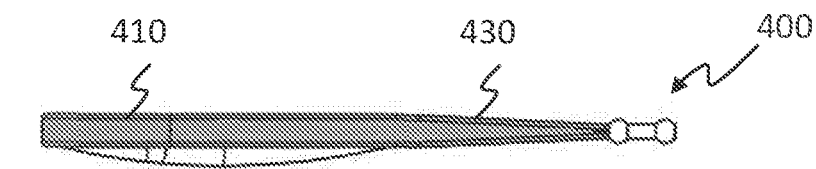
Figure 7D:

FIGS. 7A-7E depict different variations of the platform 410 and extending member 430 of a conception aid 400. In some variations, as depicted in FIGS. 7A and 7B, the platform 410 and extending member 430 may include a curvature along a longitudinal axis. The curvature can be a positive or negative curvature. In some variations, the height of the extending member 430 may decrease or increase along the length of the conception aid 400. In some variations, the height of the platform 410 may decrease or increase along the length of the conception aid 400.

Figure 7E:
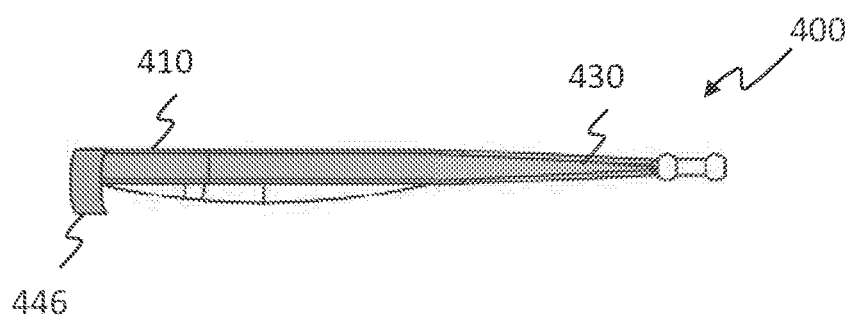

As depicted in FIG. 7E, in some variations, the conception aid 400 may include an anchoring element 446 at the proximal end. The anchoring element 446 may be useful for anchoring the conception aid 400 in a desired position within the vaginal canal, for example, until the device is moved by the user.

Figure 8A:
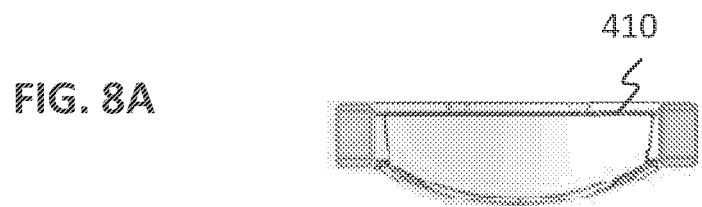
FIGS. 8A-8C depict a front cross-sectional view and two top plan views, respectively, of further variations of a platform region of a conception aid.
Figure 8B:
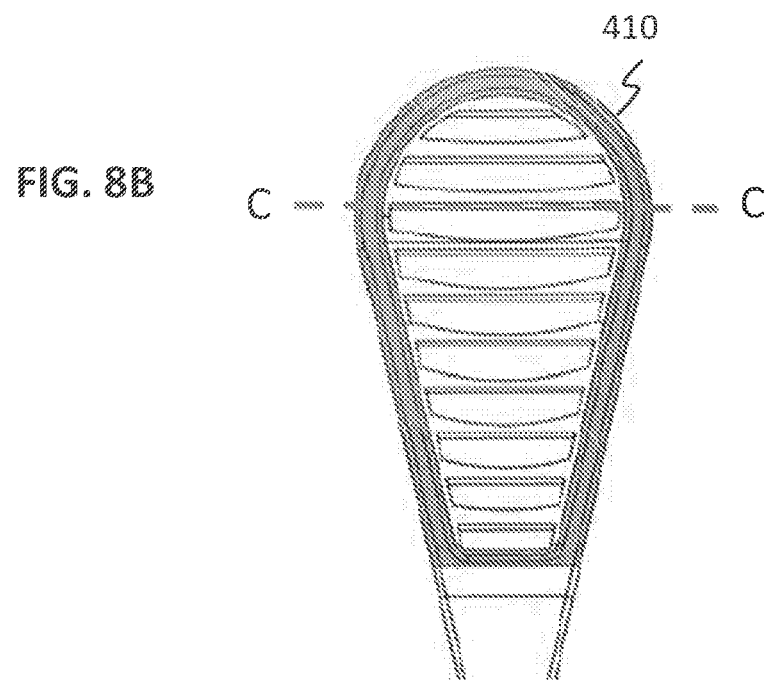
Figure 8C:
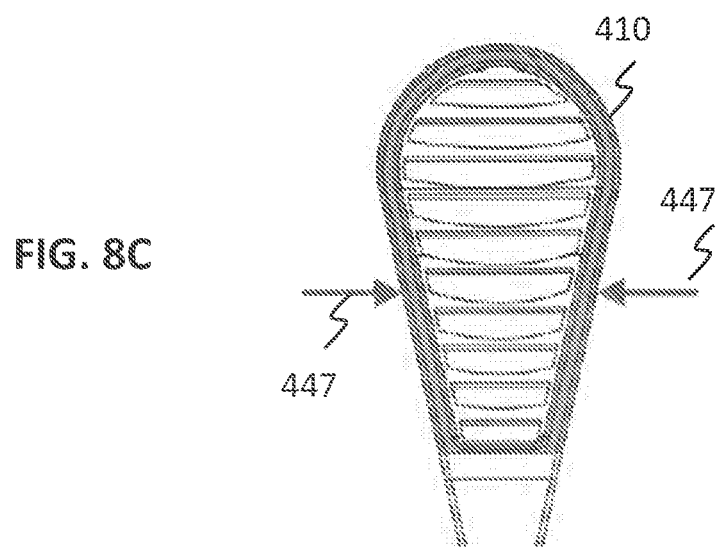

FIGS. 8A-8C depict a front cross-sectional view and two top plan views, respectively, of further variations of a platform 410 region of a conception aid. FIG. 8A shows a cross-sectional view taken along line C-C of FIG. 8B. As depicted in FIG. 8A, the platform 410 may have a rectangular cross-sectional shape. In some variations, the corners of the rectangle may be filleted. In some variations, the cross-sectional shape may be square, circular, elliptical, triangular, or a combination of any suitable shapes. In some variations, the cross-sectional shape and/or dimensions may vary at different points along the conception aid.

FIG. 8C depicts the top plan view of a variation of a conception aid having compressible features. In some variations, the conception aid may be constructed such that that platform 410 can compress, such as in the directions indicated by arrows 447, when compressed forces are applied. For example, the platform 410 may include cuts to facilitate such compression. The platform 410 may additionally or alternatively compress by fastening the platform 410 through a string, elastic string, rigid holder, or any other suitable mechanism In some variations, the conception aid, or regions of the conception aid, such as the platform 410, may compress in the directions indicated by arrows 447, to conform to the shape of the female reproductive tract when inserted into the vagina.

The conception aid may be formed from any suitable biocompatible materials, or any combination of suitable biocompatible materials. In some variations, the conception aid may be constructed from non-woven materials. The conception aid may, for example, be formed from silicone, polyurethane, and/or any combination of other suitable soft and/or hard materials. For example, the conception aid device may be flexible due to including flexible materials (e.g., silicone, or a suitable material having between about 10 and about 90 HA Shore hardness, etc.) and/or including flexing features (e.g., cutouts such as channels 124). All features (e.g., platform, extending member) could be integrally formed such as through injection molding or the like, or some may be formed separately and joined (e.g., mechanically fastened, thermally joined, etc.). Some features may be movable on the device, or removable from the device, such as, for example, the stopper element described further herein when referring to FIG. 13. In some variations, some features may formed from different materials. For example, the spine and/or extending member could be formed from a stiffer material and overmolded with a softer material forming the platform.

In some variations, the conception aid may be treated with a finishing, such as a lubricious coating, hydrophobic coating, or hydrophilic coating. For example, the surfaces of the conception aid may have a low coefficient of friction to help ease (and/or make more comfortable) the insertion of the device into the vaginal canal and/or ease (and/or make more comfortable) the passage of a penis over the device. In some variations, the low coefficient of friction is attained through the lubricious surface coating and/or surface finishing. In some variations, at least a portion of the surfaces of the conception aid may be hydrophilic and/or at least a portion of the surfaces of the conception aid may be hydrophobic. The variation in hydrophilicity or hydrophobicity may affect the wetting properties or flowability of the semen, which may help to trap semen on the surface of the conception aid and within the region near the cervical opening.

Sperm Capturing and Guiding Features

Figures 9A, 9B:
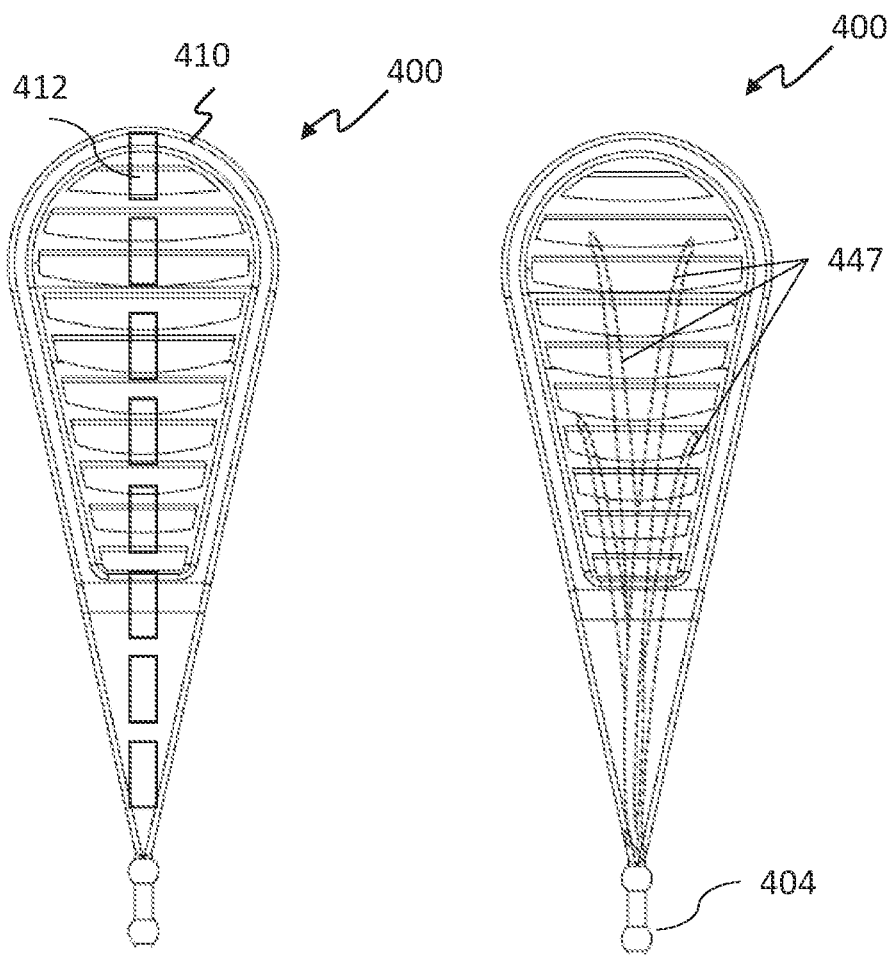
FIGS. 9A and 9B depict top plan views of variations of a conception aid having a spine, and connecting channels, respectively.

FIGS. 9A and 9B depict top plan views of variations of a conception aid 400 having a spine 412, and connecting channels 447, respectively. As depicted in FIG. 9A, a spine 412 may extend throughout the length of the conception aid 400, which may help to add structure and stability to the device by being rigid. In some variations, the spine 412 may be rigid in the tensile and compressive directions. The spine 412 may, for example, include a thicker and/or wider portion of the same material as the platform 410, and/or may be formed from a more rigid material than the platform 410 to improve structural support to the conception aid 400.

As depicted in FIG. 9B, a conception aid 400 may include connecting channels 447. In some variations, the connecting channels 447 may gather or connect, such as at or near the distal end 404 of the conception aid. The connecting channels 447 may be useful for allowing the introduction of new fluids, agitation of fluids, or modification of a microenvironment in the conception aid 400, and may also help to enhance the transport of sperm from the device to the cervix.

Figure 10A:
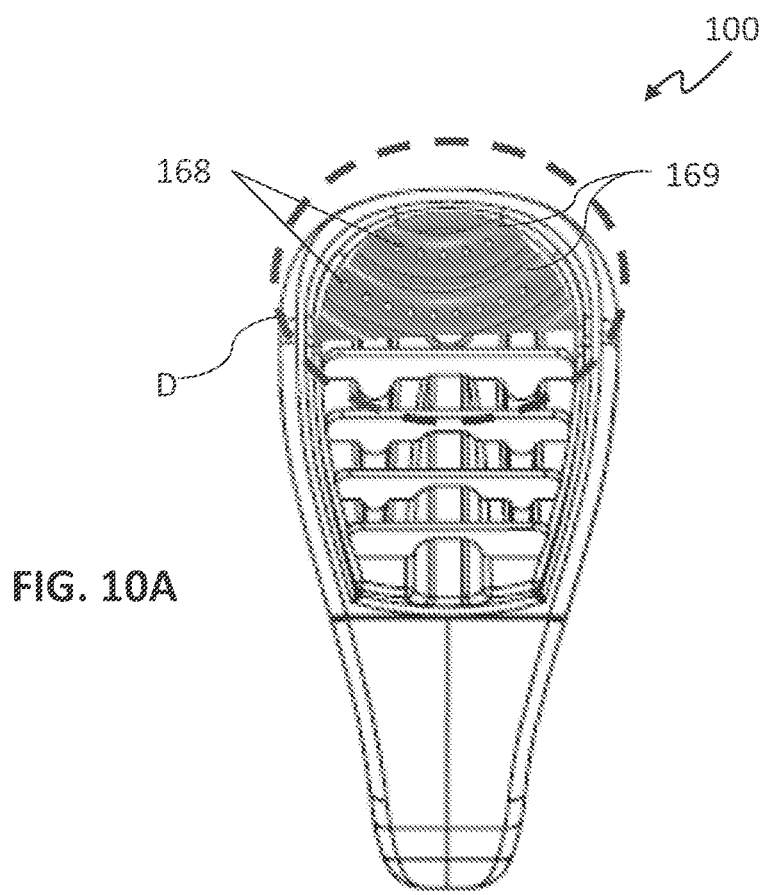
FIGS. 10A and 10B depict a top plan view and a side view, respectively, of a variation of a conception aid having further structures to improve sperm trapping.
Figure 10B:
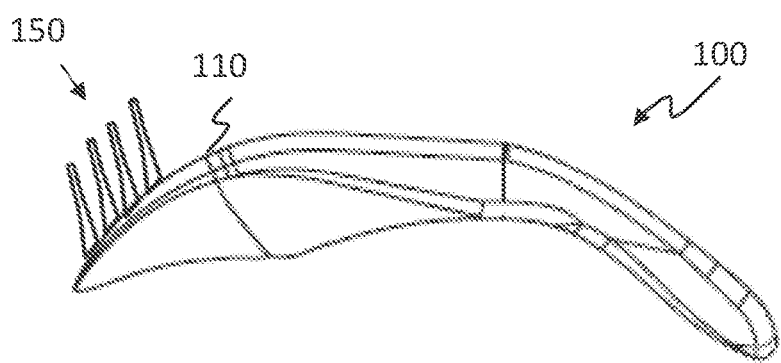

FIGS. 10A and 10B depict a top plan view and a side view, respectively, of a variation of a conception aid 100 having further structures to improve sperm trapping. In some variations, a conception aid 100 may include holes 168 in sinusoidal structures 169, shown within region D of FIG. 10A. The holes 168 and sinusoidal structures 169 may be constructed such that the area of the conception aid 100 depicted in region D of FIG. 10A can further improve sperm trapping. In some variations, a conception aid 100 may include filaments arranged as hair-like structures 150. These filaments or hair-like structures 150 may extend upwards from the platform 110, and may be useful for guiding sperm towards and into the cervical canal. The sperm may be guided along the hair-like structures 150 by capillary action, for example.

FIGS. 11A-11K depict perspective views of various examples of the platform region of a conception aid. The platform 410 may include one or more capturing elements configured to collect semen or sperm. The platform 410 may include any suitable combination of such features for facilitating the capturing and pooling of semen, for example. Thus, within the platform 410, a collection region may be formed. The platform 410 may also include any suitable combination of features for facilitating the guiding of sperm towards the cervix, for example.

Figure 11A:
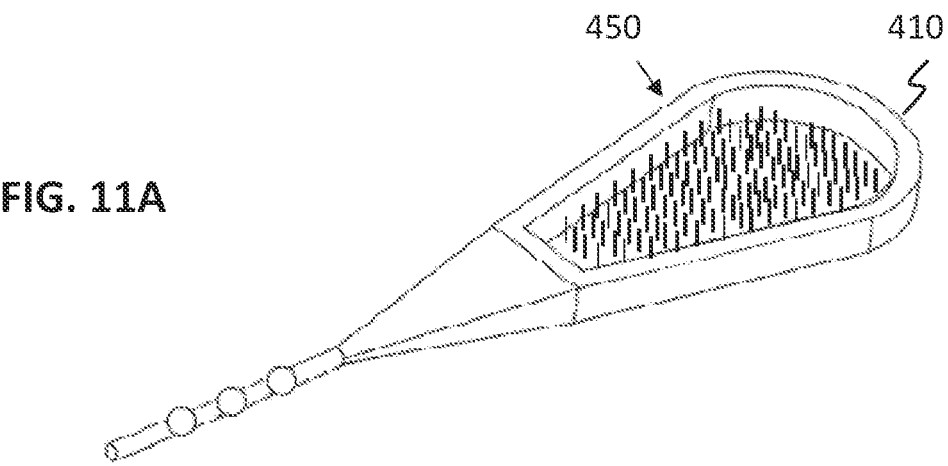
FIGS. 11A-11U depict perspective views of various examples of the platform region of a conception aid. The conception aid may include any feature or combination of features disclosed herein for aiding in capturing semen.

In some variations, such as the example depicted in FIG. 11A, a conception aid may include hair-like structures 450 or lamella or other filaments within the platform 410. The hair-like structures 450 may help to capture semen via capillary action. It should be understood that although the hair-like structures 450 are depicted within the platform 410 of FIG. 11A, the hair-like structures 450 may be included on any surface or any combination of surfaces of the conception aid.

Figure 11B:
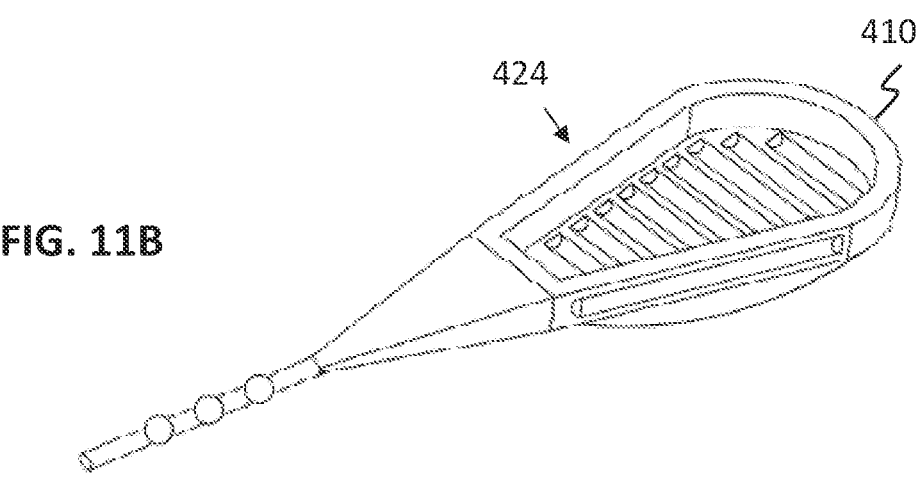

In some variations, such as the example depicted in FIG. 11B, a conception aid may include channels 424 or lamella to help capture semen via capillary action or vacuum suction. It should be understood that although the channels 424 are depicted within the platform 410 of FIG. 11, the channels 424 may be included on any surface or any combination of surfaces of the conception aid.

Figure 11C:
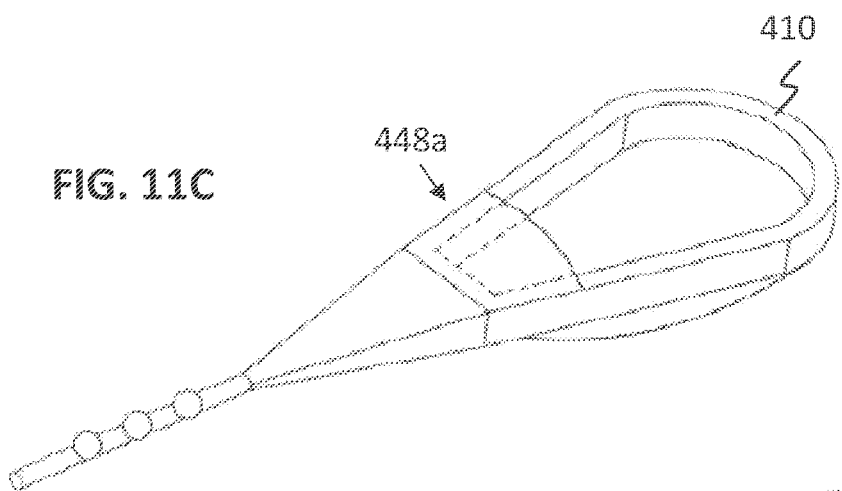
Figure 11D:
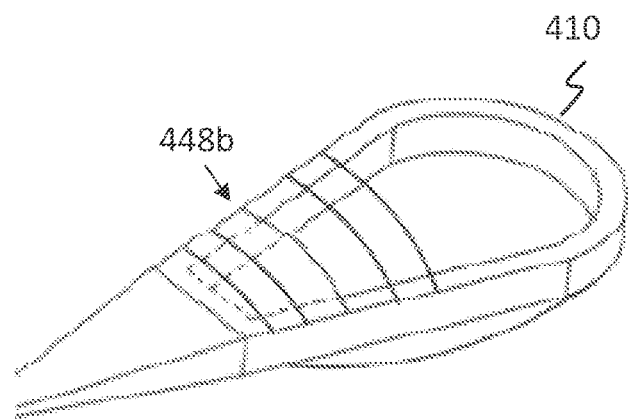

In some variations, such as the examples depicted in FIGS. 11C-11D, a conception aid may include a pocket-like feature (referred to herein as a "pocket-like feature" or "pocket") 448a or 448b within the platform 410. The pocket may be useful for containing captured sperm. The pocket may be a single pocket such as 448a, or may be multiple pockets 448b stacked on top of one another to contain the captured semen. It should be understood that any surface of the conception aid may also include a pocket or multiple stacked pockets.

Figure 18A:
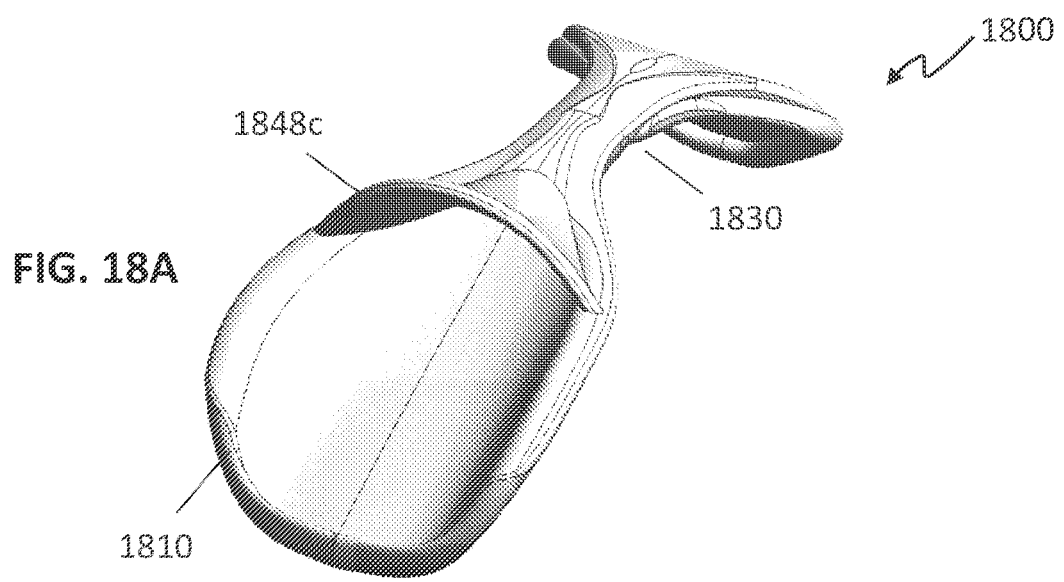
FIGS. 18A-18C depict a front perspective view, a side view, and a front elevation view, respectively, of a conception including a pocket.
Figure 18B:
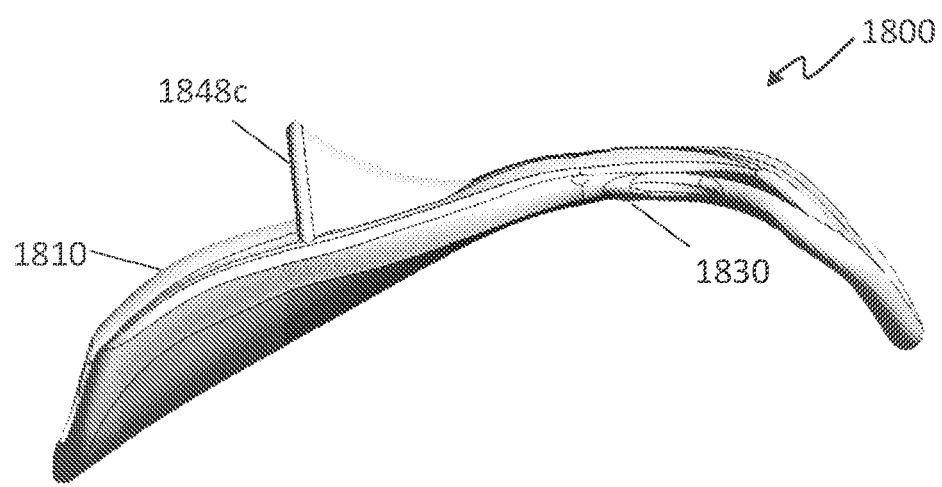
Figure 18C:
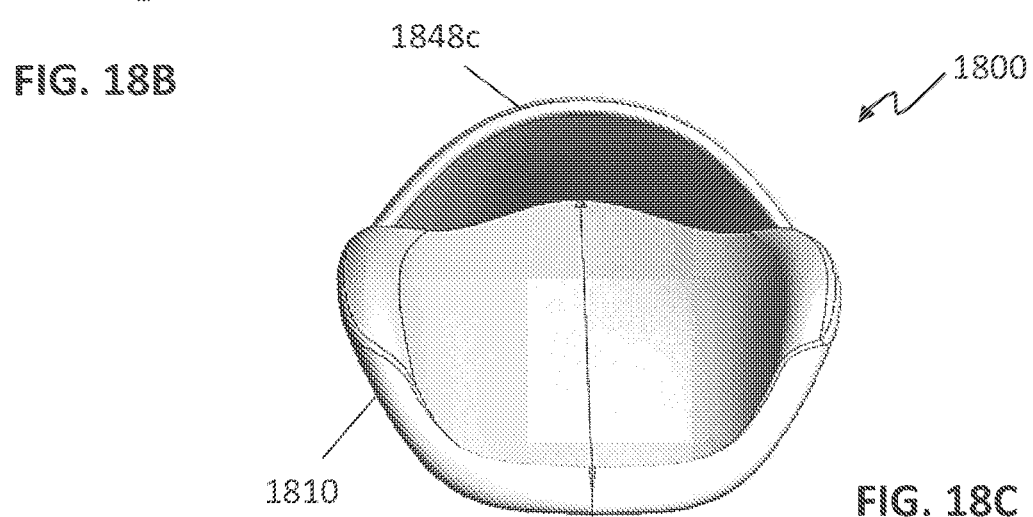

FIGS. 18A-18C depict a front perspective view, a side view, and a front view, respectively, of another variation of a conception aid 1800, wherein one or more capturing elements of the conception aid includes a pocket 1848c. In some variations, a pocket 1848c may provide a barrier between the platform 1810 and the extending member 1848c, as best shown in FIG. 18C. For example, the pocket 1848 may include an arched opening that may engage a vaginal wall such that the platform 1810 and pocket 1848c may collectively provide a barrier or other seal to contain semen and prevent the semen from exiting the vagina. The pocket may be flexible (e.g., to provide vaginal entry of a penis during intercourse). The pocket 1848c may have a thickness of between about 0.5 mm to about 3.5 mm, or about 0.8 mm to about 3 mm. In some variations, the pocket 1848c has a thickness of about 2 mm.

Figure 11E:
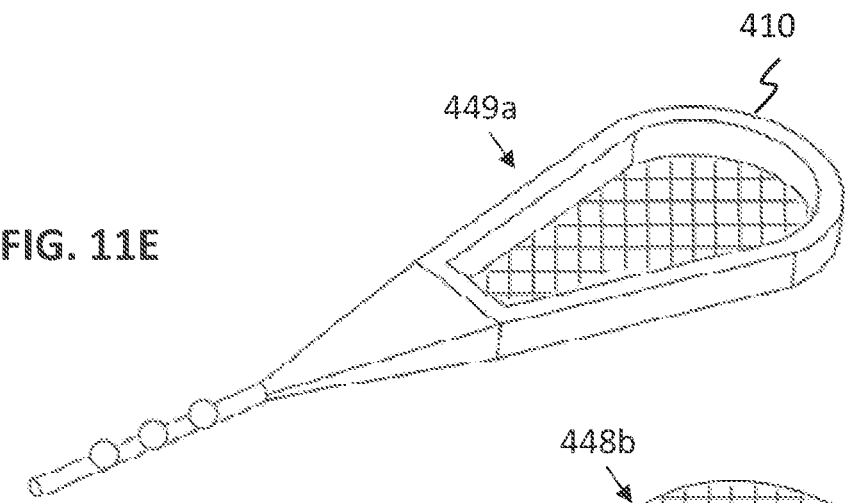
Figure 11F:
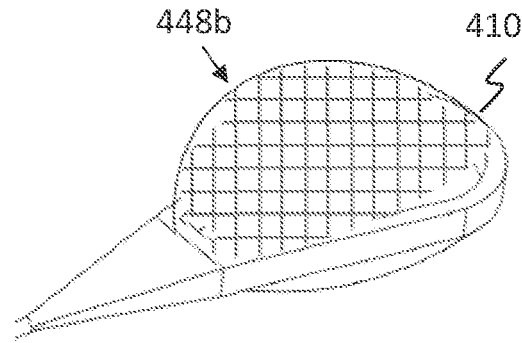

In some variations, such as the examples depicted in FIGS. 11E-11F, a conception may include filaments arranged as a mesh 449a or 449b within the platform 410, which may help to capture the semen via capillary action. In some variations, the platform 410 may be constructed from the mesh, shown by 449b. It should be understood that the mesh 449a or 449b may be included on any surface or combination of surfaces of the conception aid.

Figure 11G:
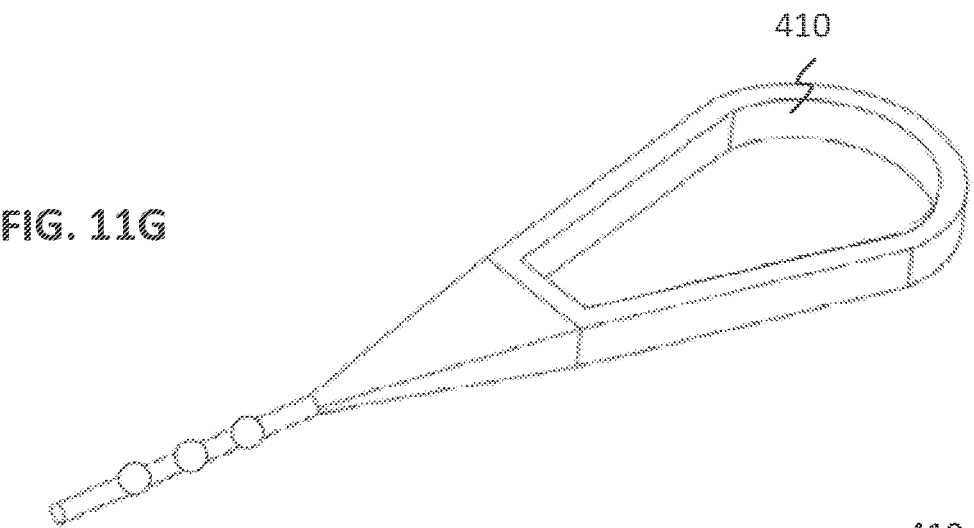
Figure 11H:
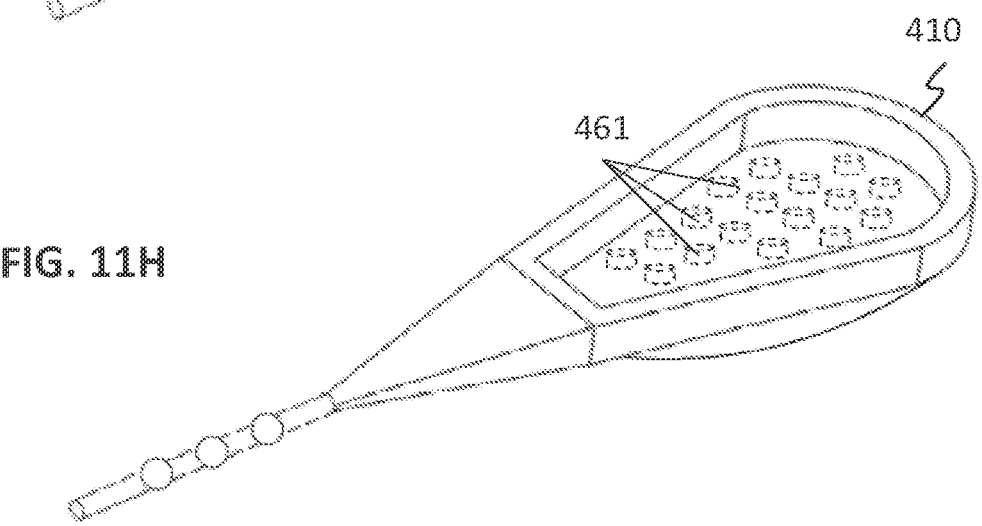

FIG. 11G depicts an example of a conception aid wherein the platform 410 provides a hollow cavity within which semen can be captured. It should be understood that the conception aid can be included with a platform 410 having only a hollow cavity, or any other features or combination of features. For example, as depicted in FIG. 11K, the platform 410 may include wells 461, which may include a cylindrical shape. The wells 461 can help to capture semen via capillary action or vacuum suction. An exemplary range of the well depth is about 3 to about 7 millimeters (mm). As another example, the wells 461 may be hemi-spherical, or any other suitable shape for capturing semen.

Figure 11I:
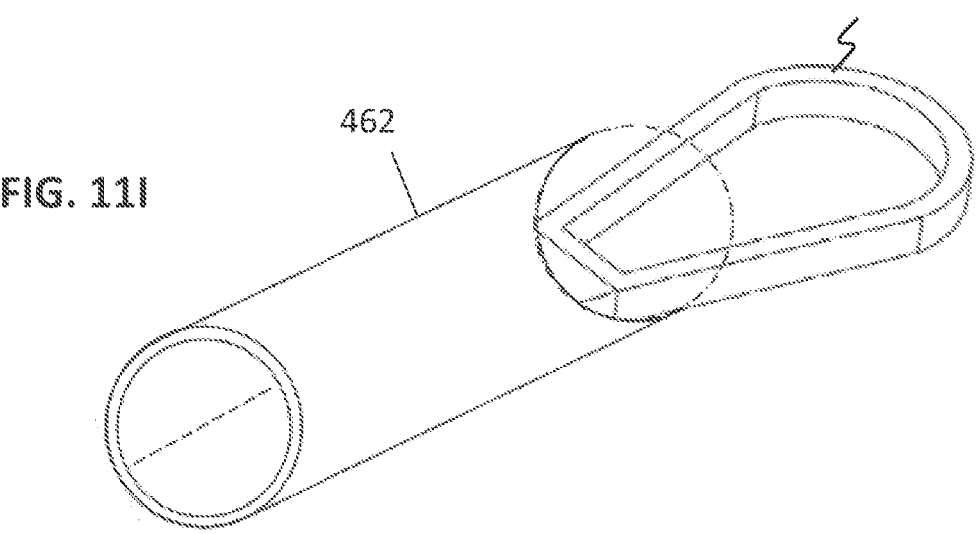

In some variations, as shown in FIG. 11I as an example, the conception aid may also include a receptacle member 462 for holding captured semen. The conception aid may thus include one or more elements for allowing the closing or opening of the receptacle. The elements may include balloons, valves, pull-strings, elastic material, or any other suitable elements.

Figure 11J:
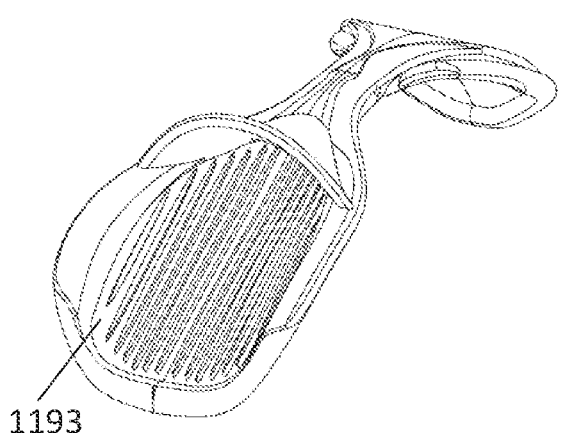
Figure 11K:
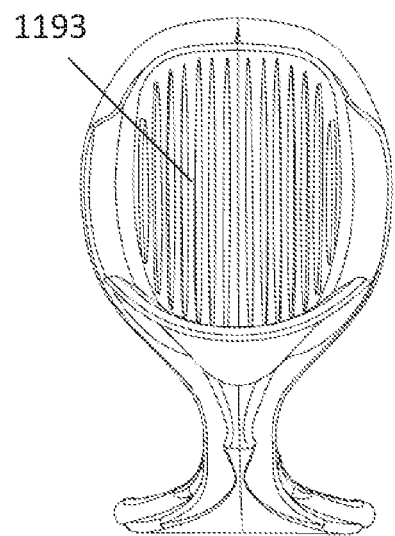
Figure 11L:
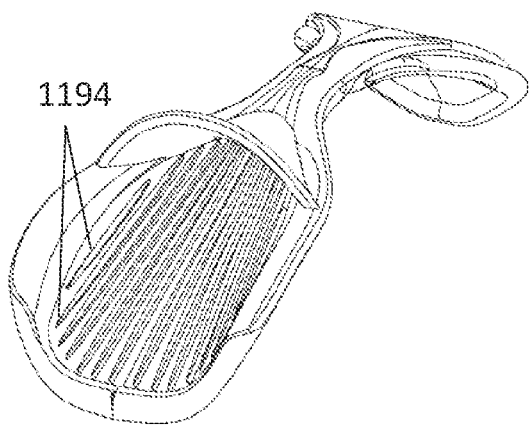
Figure 11M:
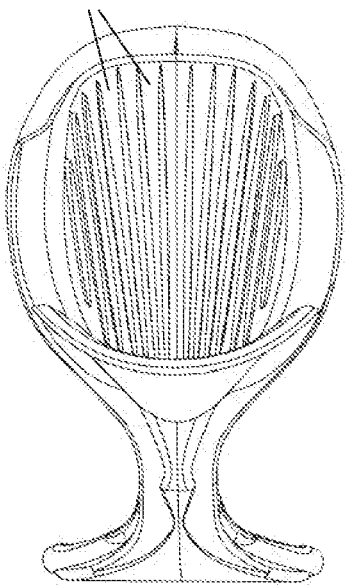

FIGS. 11J-11K depict a perspective view and a top plan view, respectively, of a variation of a conception aid having longitudinal channels 1193, and FIGS. 11L-11M depict a perspective view and a top plan view, respectively, of a second variation of a conception aid having longitudinal channels. In such variations, a conception aid may include a plurality of longitudinal channels, which may also include longitudinal recesses. In such variations, a protrusion 1194 may also be provided between each channel of the plurality of longitudinal channels. These channels may be substantially straight and parallel, such as in the first variation of a conception aid having longitudinal channels depicted in FIGS. 11J-11K. The longitudinal channels may help direct semen toward one or more capturing elements (e.g., pocket). As another example, some or all of these channels may be angled relative to a longitudinal axis of the conception aid, such that they fan outwards or radiate laterally from a distal end of the platform, such as in the variation of a conception aid having longitudinal channels depicted in FIGS. 11L-11M. The angled channels may help funnel semen toward one or more capturing elements (e.g., pocket). For example, in some variations at least one of the channels may be angled between about 1 degree and about 30 degrees, between about 1 degree and about 20 degrees, between about 1 degree and about 15 degrees, or between about 1 degree and about 10 degrees relative to the longitudinal axis of the conception aid.

Figures 11N, 11O:
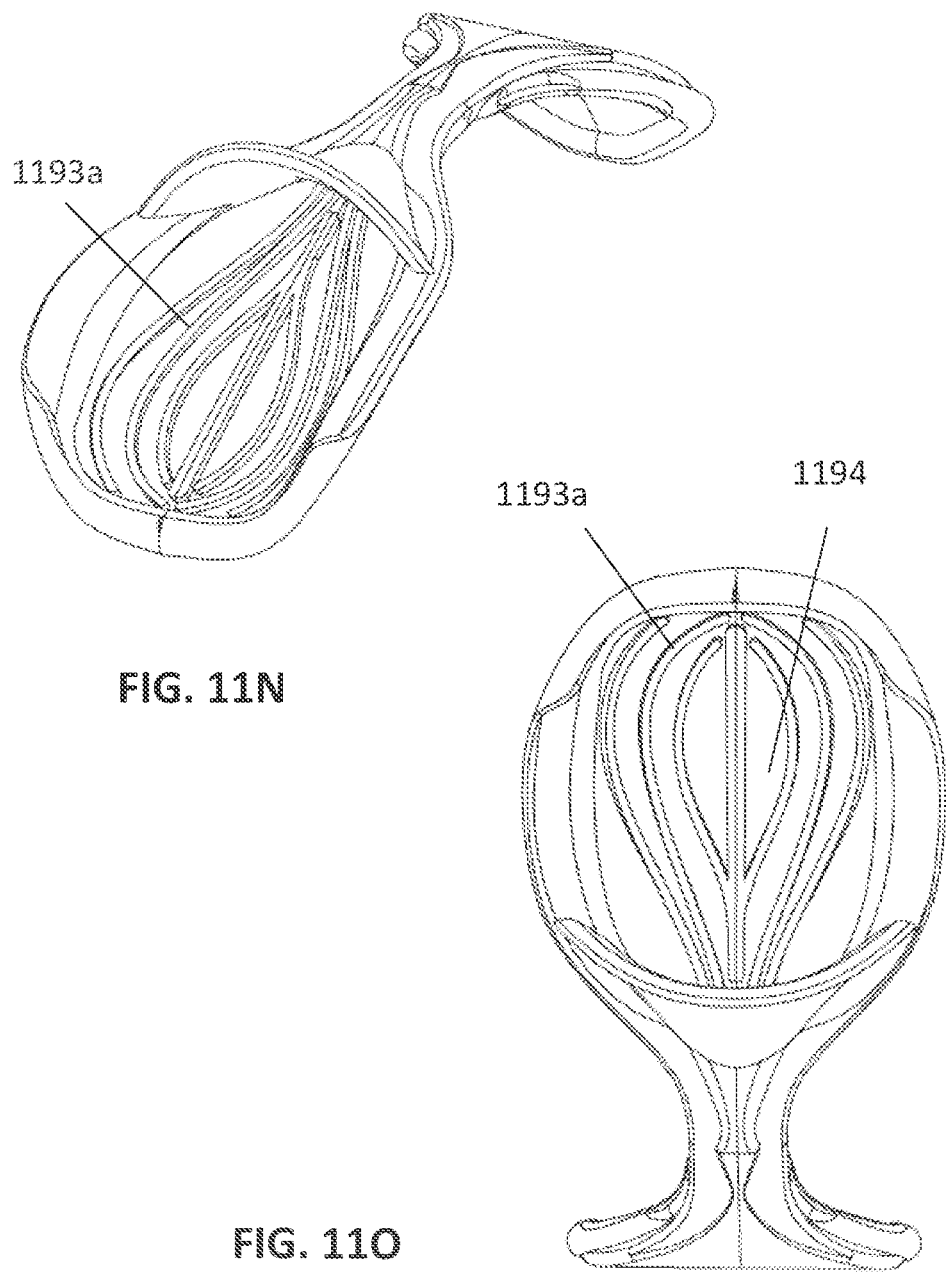

FIGS. 11N-11O depict a perspective view and a top plan view, respectively, of a variation of a conception aid having longitudinal channels 1193*a*, wherein the longitudinal channels are branched channels. Such channels may be branched or segmented, and may also be curved, such that they promote the flow of semen towards a proximal end of the conception aid, or promote a concentrated central region 1194 in which semen can be pooled. The collected pool of semen can then be placed proximate a cervix in order to aid in conception.

Figure 11P:
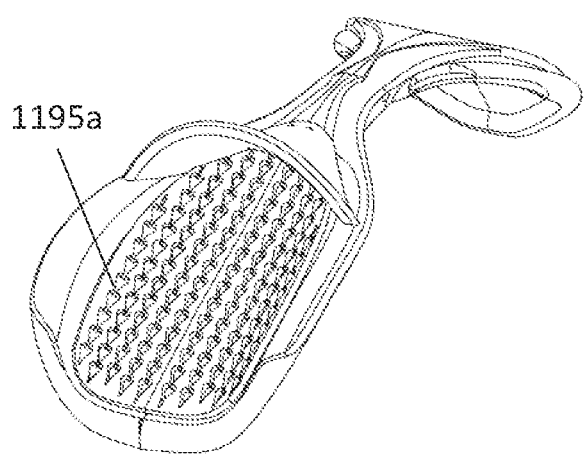
Figure 11Q:
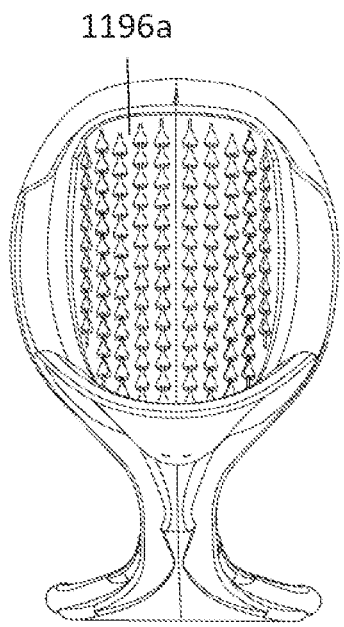

FIGS. 11P-11Q depict a perspective view and a top plan view, respectively, of a variation of a conception aid having channels 1195*a* with ratcheting features to help promote unidirectional swimming of sperm cells, such as toward a proximal end of the conception aid. The channels 1195*a* may, for example, include heart-shaped segments (with pointed end directed toward a proximal end of the conception aid) or other suitable ratcheting features.

Figure 11R:
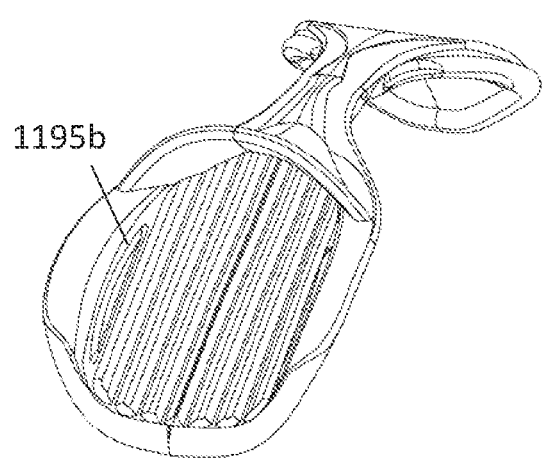
Figure 11S:
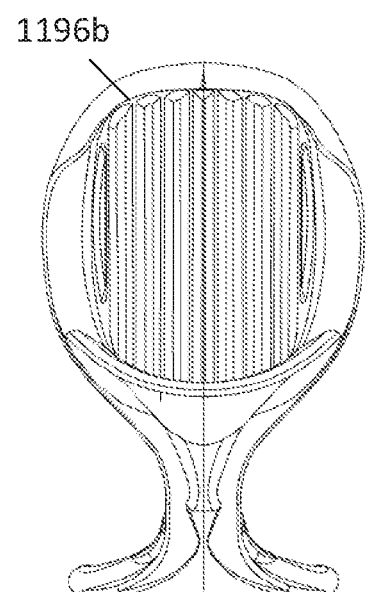

FIGS. 11R-11S depict a perspective view and a top plan view, respectively, of a variation of a conception aid including bumps 1195*b*. The bumps 1195*b* may be elongated and rounded or beveled along their length, and may facilitate the swimming of sperm cells in the tracts or recesses that are formed between these rounded bumps, indicated by 1196*b*.

FIGS. 12A-12D depict top plan views of a variation of a conception aid platform 410 and further variations of sperm capturing features within the platform 410. As shown as an example in FIG. 12A, a platform 410 may include a front ramp 463 at the proximal end of the conception aid. The frontal ramp 463 may be useful for capturing semen via scooping action. It should be understood that the frontal ramp 463 may also include any feature or combination of features disclosed herein for assisting in capturing semen.

As depicted in FIG. 12B, and as described further herein when referring to FIG. 4A, a platform 410 may include lateral ridges 422. The platform 410 may also include a string 464 weaved through the lateral ridges 422 such that the lateral ridges 422 are held open during use, and to further assist in semen capture.

Figure 12C:
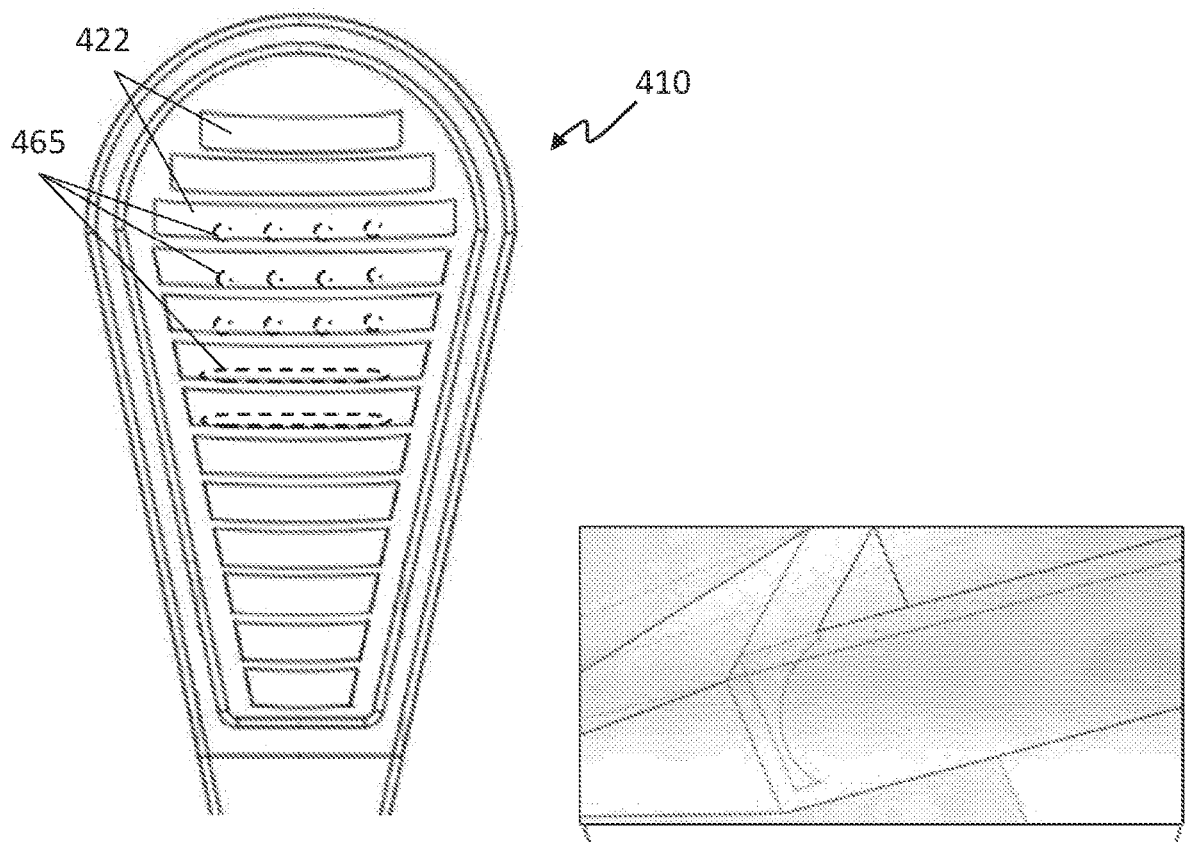

As depicted in FIG. 12C, the platform 410 may further include bumps 465 underneath the lateral ridges 422. These bumps 465 may also assist in keeping the lateral ridges 422 open, and may be straight rods along the ridges, or may be small spherical bumps, for example. The bumps 465 may be of any other suitable shape and size to assist in keeping the lateral ridges 422 open, for example.

FIGS. 17A-17B depict another variation of bumps or filaments on the platform 1710 of a conception aid 1700, which may be peg-like structures 1773. It should be understood that a conception aid may be provided with one or more bump or filament structures. When the conception aid is provided with a plurality of filaments, such as peg-like structures 1773, the plurality may be arranged in a formation suitable for facilitating the travel of sperm to a desired location, such as towards the proximal end of the conception aid. As shown in FIGS. 17A-17B, the peg-like structures 1773 may be arranged in a generally spiral formation, having an open outlet 1773*a* at the proximal end 1702 of the platform 1710. The spiral formation and the open outlet 1773*a* may facilitate the traveling of the sperm into a desired direction; for example, the sperm may be aided in traveling towards the proximal end and flow out of the spiral formation through the open outlet 1773*a*.

Figure 12D:
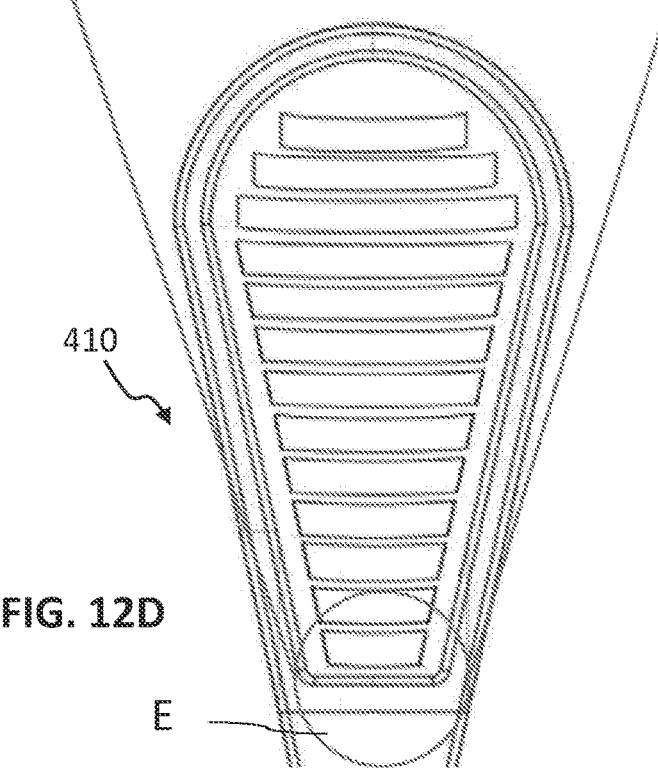

FIG. 12D depicts a platform 410 and a detailed enlarged view of a bottom perspective view of region E, showing that the platform 410 may include a slight undercut at the distal end of the platform. The undercut may aid in improving the retention of captured semen at the distal end of the platform 410, for example.

Figure 11T:
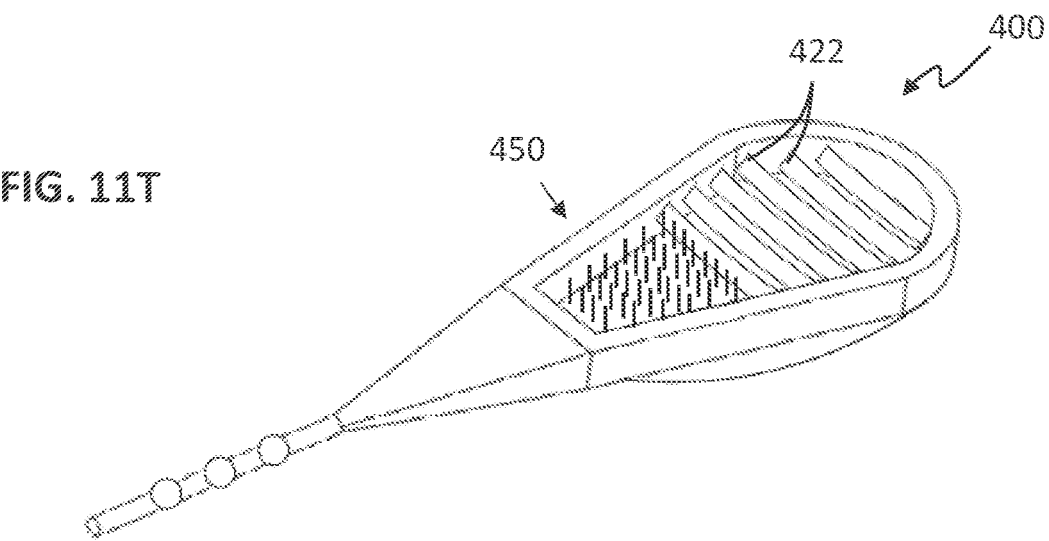
Figure 11U:
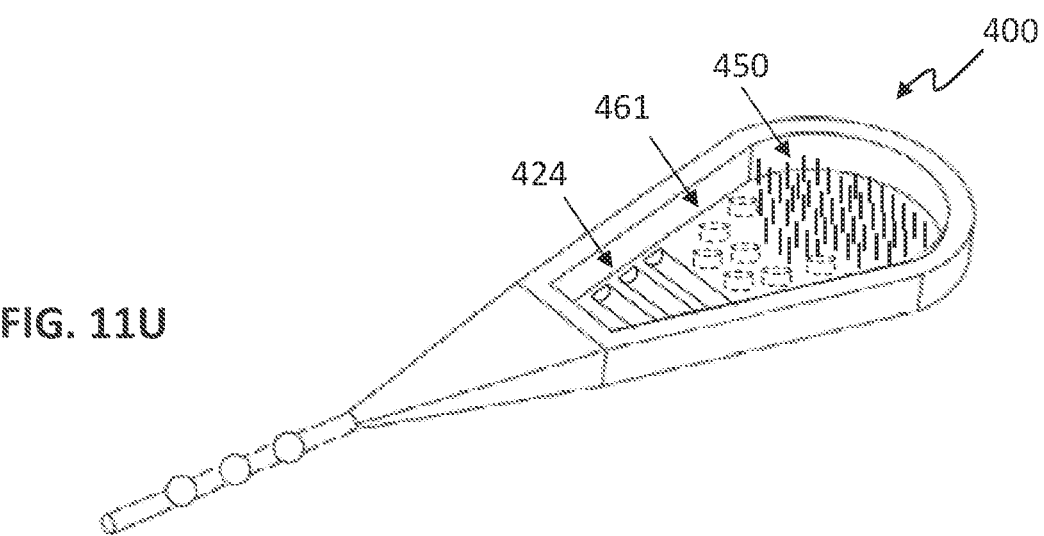

It should be understood that a conception aid may include any feature or combination of features disclosed herein for aiding in the capturing and/or guiding of semen. For example, FIGS. 11T and 11U depict variations of a conception aid having a combination of semen capturing features. FIG. 1I T depicts a conception aid 400 having lateral 422 and hair-like structures 450. FIG. 11U depicts a conception aid 400 having hair-like structures 450, wells 461, and channels 424. A combination of sperm capturing features may increase the ability of the conception aid 400 to capture and collect semen, for example.

Conception Aids for Use with a Depositing Device

Any of the conception aids disclosed herein may also be used for collection of semen by use of an additional sperm depositing device. For example, a depositing device may be used to deposit semen onto a platform of any of the conception aids disclosed herein. The depositing of semen with the use of the depositing device may be performed before or after placement of the conception aid within a vaginal canal. Any of conception aids disclosed herein may be provided with additional elements or features to aid in the use of the depositing device.

In some variations, a depositing device may be used to deposit semen onto the platform while the conception aid is external to the vaginal canal. In such variations, a user may use any suitable depositing device to collect semen onto the platform, and next positioning the conception aid within the vaginal canal. In some other variations, the conception aid may be placed into a vaginal canal prior to use of the depositing device, such that the depositing device introduces semen to the conception aid while the conception aid is internal to the vaginal canal.

Figure 19A:
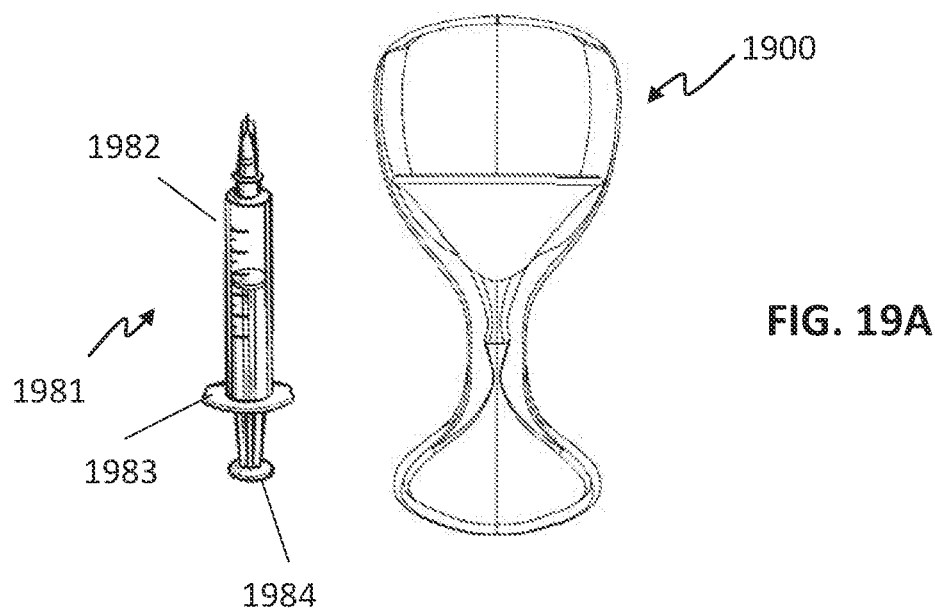
FIGS. 19A-19E depict a conception aid that can be used with a depositing device, and exemplary methods of uses of the depositing device with the conception aid.

FIG. 19A depicts an exemplary depositing device 1981 with an exemplary conception aid 1900. In some variations, a depositing device 1981 comprises a barrel or other container 1982, a handle 1983, and a plunger 1984. In some variations, a depositing device is a syringe. The depositing device may be operable by applying a force to the plunger 1984 to deposit sperm or semen from the container 1982 onto the platform 1910.

In some variations, any of the conception aids disclosed herein may be used with a depositing device 1981. The conception aid may include one or more additional elements or features to aid in the use of the depositing device, such that the conception aid can receive the depositing device (as will be further discussed when referring to FIG. 19B). In some variations, any of the conception aids disclosed herein may be used with a depositing device 1981, wherein the depositing device is placed over the conception aid during use. In such variations, the depositing device can be placed over the conception aid (as will be further discussed when referring to FIG. 19C), wherein the placement of the depositing device may be similar to placement of a penis during intercourse while the conception aid is positioned within a vaginal canal.

Figure 19B:
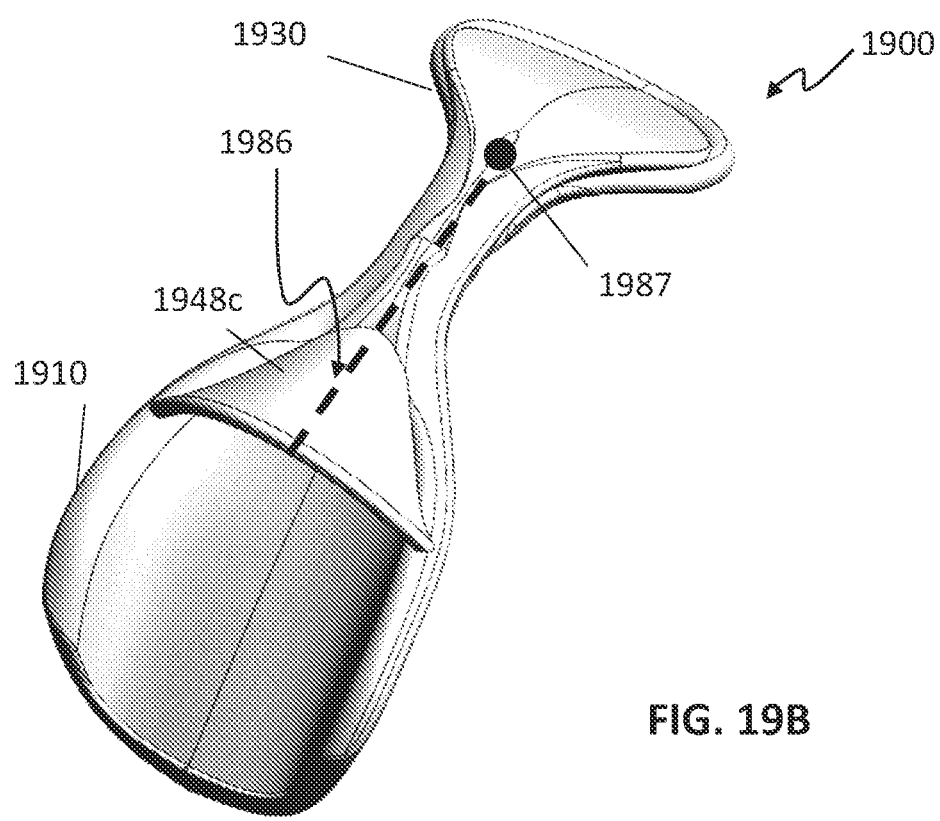

FIG. 19B depicts a conception aid 1900 that can receive a depositing device. It should be understood that, while any suitable depositing device may be used to deposit semen on the platform 1910 of the conception aid, a conception aid 1900 may also be provided with additional elements or features to receive a depositing device, such as within a lumen or cavity. The conception aid 1900 depicted in FIG. 19B is shown having an extending member 1930 coupled to a distal portion of a platform 1910, as well as a lumen, represented by broken line 1986. In some variations, the lumen further extends into at least one of the one or more capturing elements. As shown as an example in FIG. 19B, the one or more capturing elements of the conception aid may be a pocket 1948c. In such variations, the pocket 1948c may define a portion of the lumen, and the lumen may further extend into a wall of the pocket. Additionally, the pocket may provide a barrier between the platform 1910 and the extending member 1930. The lumen 1986 may be configured to receive a depositing device for depositing semen or sperm onto the platform 1910.

Figure 19C:
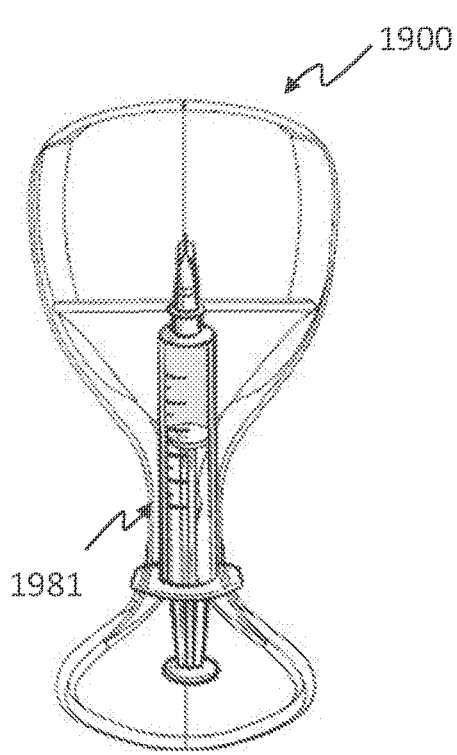
Figure 19D:
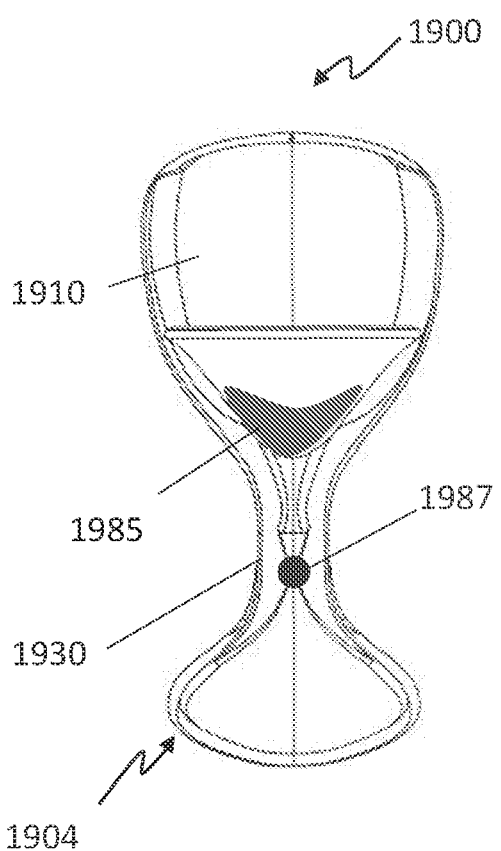

In some variations, a depositing device 1981 is inserted within the conception aid 1900 through a self-sealing valve 1987, as depicted in FIGS. 19B and 19D. The self-sealing valve include a separate component at a distal opening, at a proximal opening, or any other suitable location along the lumen, or the self-sealing valve may be formed by the surrounding flexible material of the extending member and/or the one or more capturing elements (e.g., pocket). In such variations, removal of the depositing device 1981 from the conception aid 1900 causes the self-sealing valve to close, such that a barrier is formed and maintained between the platform 1910 and the extending member 1930. The automatic closure of the valve may further enable collected semen to remain within the pocket 1948c, as shown in FIG. 19D. In such variations, a portion of the lumen is openable by insertion of the depositing device, and sealed by removal of the depositing device. In some variations, multiple self-sealing valves may be included at an opening or other suitable location along the lumen. Additionally or alternatively, the conception aid 1900 may include one or more actuatable valves. For example one or more actuatable valves may be configured to close the lumen in response to actuation of a user interface device and/or configured to open the lumen in response to actuation of a user interface device. In some variations, the valve may be biased to a default closed state and opened in response to actuation of a user interface device. Suitable user interface devices for actuating a valve of the lumen may include, for example, a button, a slide, a switch, etc. Furthermore, a valve may be actuated by manually pinching the lumen closed, and material surrounding the lumen may be deformable in response to the pinching force to remain closed.

In some variations, the lumen may vary in diameter along the extending member 1930. For example, the lumen may narrow in diameter as it extends in the distal direction toward and/or along the extending member 1930. Additionally or alternatively, the lumen may narrow in diameter as it extends in the proximal direction toward and/or along the one or more capturing elements. In some variations, the lumen may have a substantially similar diameter throughout its length. In some exemplary variations, the diameter of the lumen may be between about 0.5 mm to about 2.5 mm. In some exemplary variations, the diameter of the lumen is about 2 mm.

It should be understood that any conception aid including elements such as a lumen for receiving a depositing device could also be used by placing the depositing device over the conception aid, as depicted in FIG. 19C, or by insertion of the depositing device into the lumen.

FIG. 19C depicts an exemplary depositing device 1981 shown positioned over a conception aid 1900. It should be understood that any of the conception aids disclosed herein could be used with a depositing device. A depositing device can be placed over the conception aid, similar to the placement of a penis when the conception aid is placed in a vaginal canal and used during intercourse (as depicted in FIGS. 3A and 5A). The depositing device can then be operated, such as by applying a force to a plunger of the depositing device, to collect semen onto the conception aid, such as onto the platform of the conception aid.

FIG. 19D depicts an exemplary conception aid 1900 having a pocket 1948c, after collection of semen 1985. In some variations, a conception aid 1900 comprising a pocket 1948c may be used for collecting semen, deposited using a depositing device 1981. After the semen is deposited onto the platform 1910, the pocket 1948c can provide a barrier such that the collected semen 1985 does not flow back towards a distal portion of the conception aid.

Figure 19E:
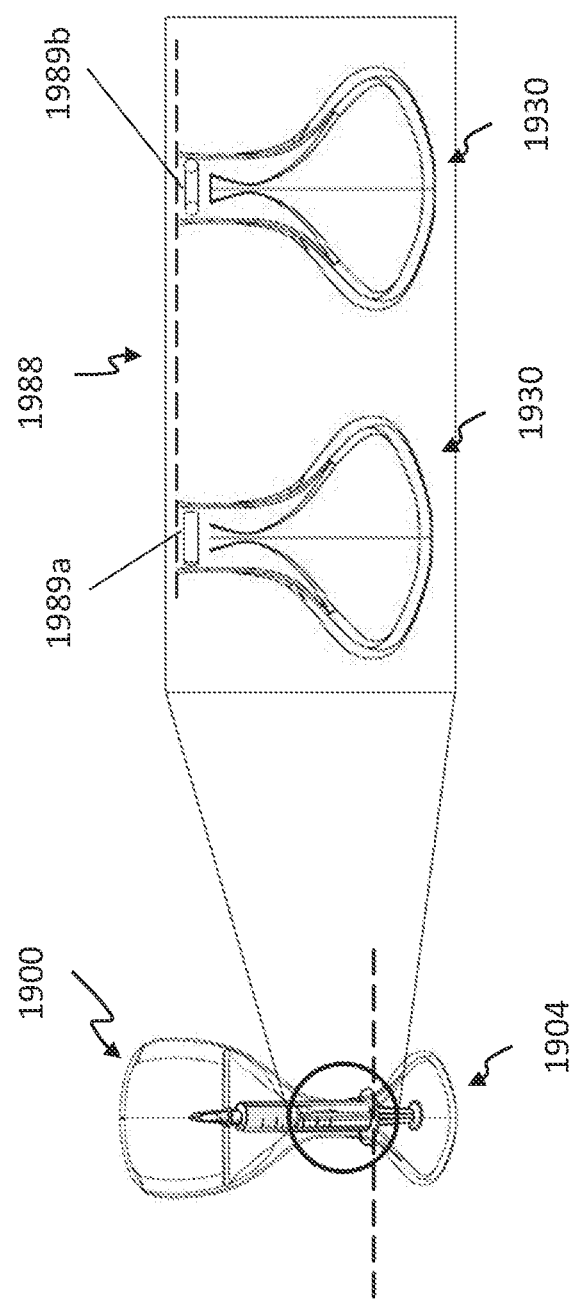

FIG. 19E depicts an exemplary conception aid 1900, and a detailed enlargement of a distal portion 1904 of the conception aid, shown by 1988, wherein the extending member 1930 comprises a stop guide 1989a or 1989b. The stop guide may function at least in part as a depth indicator to a user, such that a user can be provided with a tactile and/or visual guidance for placement of the depositing device. The stop guide may be configured to guide insertion of a depositing device within the lumen (as depicted in FIG. 19B), or over a conception aid (as depicted in FIG. 19C). In some variations, the stop guide is configured to abut a handle (shown by 1983 in FIG. 19A) of the depositing device. The stop guide may be configured to guide depth of insertion of the depositing device within the lumen or over a conception aid. For example, in some variations, the stop guide may be a protrusion 1989a, or a groove or indentation 1989b, and an abutment of the depositing device handle 1983 can indicate to a user that a correct placement of the depositing device has been achieved. In some variations, one or more stop guides or depth indicators are provided, such that tactile and/or visual feedback or guidance is provided to the user for a variety of depths of the depositing device within or over the conception aid. In some variations, the stop guide can aid a user in placing a depositing device such that a tip of the depositing device extends onto the conception aid platform. This may aid in collection of semen or sperm onto the platform.

Removal Member

Figure 13A:
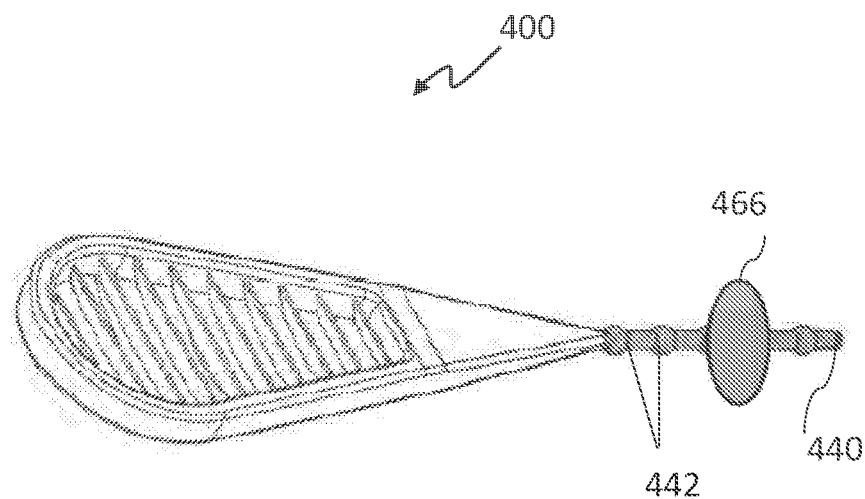
FIG. 13A depicts a side perspective view of a conception aid including a stopper element. The stopper element may assist in removal of the conception aid, or may also adjust the overall length of the conception aid device.

FIG. 13A depicts a side perspective view of a conception aid 400 including a stopper element 466. The stopper element 466 may be included along the removal member 440, for example. In some variations, a conception aid 400 may include the stopper element 466 that can be moved along the textural elements 442, which can allow for the overall length of the conception aid 400 to be adjusted according to the needs or preferences of the user. The stopper element may also assist in the removal of the conception aid from the vaginal canal, for example. The stopper element 466 may also be removable from the conception aid 400.

It should be understood that the removal member 440 may be sufficiently long and flexible such that it may remain in place, unobtrusively, during intercourse, but may be easily accessed by the user once the conception aid is to be removed from the vaginal canal. The user may then manually remove the conception aid by grasping the removal member 440, or by grasping the stopper element 466 on the removal member 440.

Figure 13B:
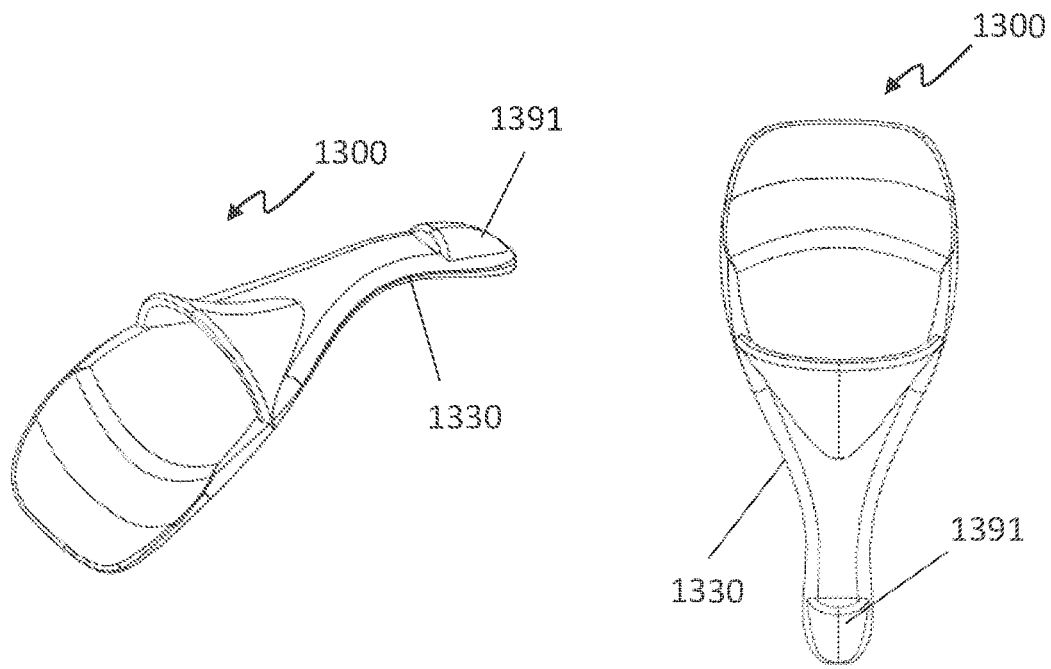
FIGS. 13B-13C depict a perspective view and a top plan view, respectively, of a conception aid having a removal element.
Figure 13C:
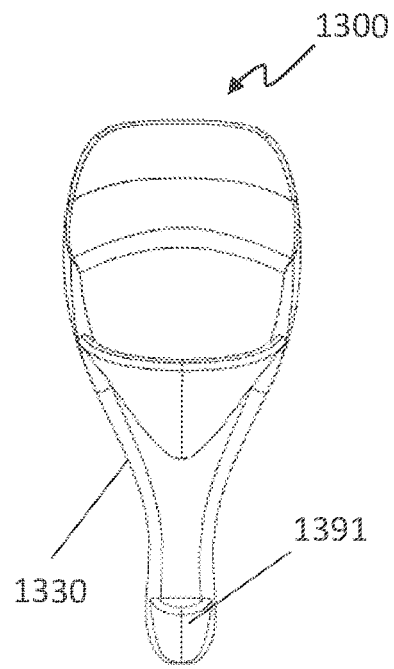

FIGS. 13B-13C depict a perspective view and a top plan view, respectively, of another exemplary conception aid 1300 having a removal element for ease of removal of the conception aid. The exemplary conception aid 1300 is shown having a tapered shape at a distal portion of the extending member, as an example. In some variations, the removal element is a grip 1391, provided on an extending member of the conception aid at a distal end 1304 of the conception aid. The grip may help a user in grasping the conception for easier removal of the device from a vaginal canal. The grip 1391 may be raised from the surface of the extending member 1330, such that a user can more easily hold the conception aid device.

Examples

Figure 15A:
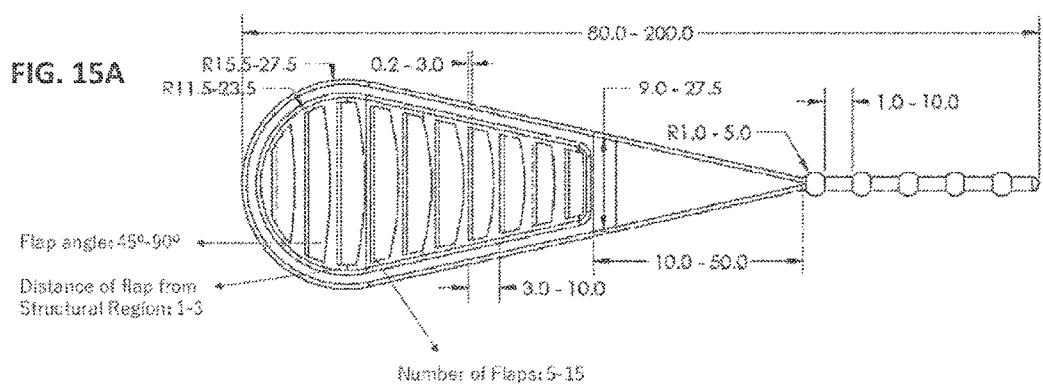
Figure 15B:
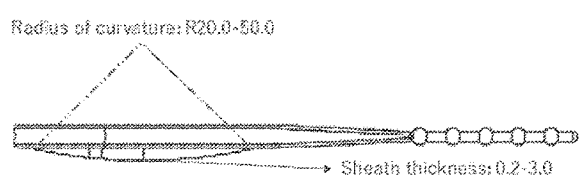
Figure 15C:
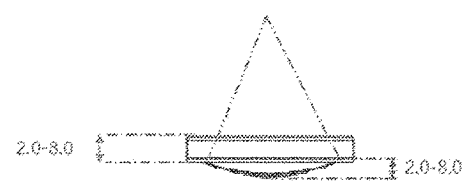

FIGS. 14A-14B and 15A-15C depict schematic illustrations of variations of a conception aid having exemplary dimensions. FIGS. 14A and 14B are a top plan view and a side cross-sectional view, respectively, of a variation of a conception aid, as is also shown in FIGS. 1A-1F. FIGS. 15A-15C are a top plan view, a side view, and a front view, respectively, of a variation of a conception aid, as is also shown in FIGS. 4A and 4B.

As depicted as an example in FIG. 14A, the conception aid may have an exemplary length of about 85 mm, or about 75 mm to about 95 mm. The conception aid may have an exemplary width at the proximal end of about 40 mm, or about 30 mm to about 50 mm. The conception aid may narrow to an exemplary width at the distal end of about 17 mm, or about 7 mm to about 27 mm. A center portion of the conception aid may have an exemplary width of about 23 mm, or about 13 mm to about 33 mm. An exemplary distance between lateral ridges within the platform is about 7 mm, or about 4 mm to about 15 mm. An exemplary width of each lateral ridge is about 0.8 mm, or about 0.3 mm to about 1.5 mm. It should be understood that the dimensions of each lateral ridge may vary, or may be the same. As depicted as an example in FIG. 14B, an exemplary height along a mid-portion of the conception aid is about 10.8 mm, or about 7 mm to about 12 mm. An exemplary height of the side flaps of the conception aid is about 2 mm, or about 1 mm to about 3 mm.

As shown as an example in FIG. 15A, an exemplary length of a conception aid is about 80 to about 200 mm, or about 70 mm to about 210 mm. At the widest point of the platform, an exemplary radius is about R15.5-27.5 mm, or about R10.5-30.5 mm. An interior portion of the platform may have an exemplary radius of about R11.5-23.5 mm, or about R10.5-26.5 mm. An exemplary length of an extending member is about 10 mm to about 50 mm, or about 6 mm to about 60 mm. An exemplary distance between textural elements along the removal member is about 1 mm to about 10 mm, or about 0.5 mm to about 15 mm. An exemplary width at the portion of the conception aid between the platform and the extending member is about 9.0 mm to about 27.5 mm, or about 5 mm to about 35 mm. An exemplary distance between lateral ridges is about 0.2 mm to about 3 mm, or about 0.1 mm to about 6 mm. An exemplary width of each lateral ridge is about 3 mm to about 10 mm, or about 1 mm to about 15 mm. As shown as an example in FIG. 15B, an exemplary thickness of the interior portion of the platform is about 0.2 mm to about 3 mm, or about 0.1 mm to about 6 mm. An exemplary radius of the curvature of the platform is about R20.0-50.0 mm, or about R15.0-55.0 mm. As shown as an example in FIG. 15C, an exemplary height of the conception aid at the proximal end is about 2 mm to about 8 mm, or about 1 mm to about 12 mm. An exemplary height of the platform interior portion is about 2 mm to about 8 mm, or about 1 mm to about 12 mm.

It should be understood that in some variations, a conception aid device may be sized and/or shaped for particular anatomy (e.g., generally, smaller devices may be more suitable for use in narrower vaginal canals, and vice versa). Accordingly, a conception aid device may be available in multiple sizes (e.g., small, medium, large, etc.) for use in addressing the needs in a wider population desiring assistance with conception.

Funneling Conception Aid

Generally, in some variations, a conception aid device may include a flexible funnel-like structure designed to be placed entirely or at least partially within the vaginal cavity. The device may generally include an insertion portion configured for placement into proximity to the cervix and a receptacle portion configured to receive a penis inserted within the receptacle portion. The insertion portion and receptacle portion may define and maintain a continuous lumen through the device to help ensure that any sperm deposited within the device is funneled directly to the cervix.

The device may, for example, be used in a method of assisting natural conception by positioning the insertion member in proximity to a cervical opening, and positioning the receptacle member in proximity to a vaginal opening. The insertion portion may be temporarily secured via an anchor member in proximity to the cervix such that the insertion portion surrounds or at least partially envelopes the cervix. The receptacle portion may extend from the cervix and partially or fully within the vaginal cavity such that when the penis is inserted within the vaginal cavity during intercourse, the receptacle portion may be positioned to directly receive any ejaculate.

In some variations, the device may further include at least one capturing member positioned at a distal end of the receptacle portion and configured to retain any semen ejaculated from the male. The captured semen may be guided via any number of mechanisms to transfer from the capturing member, through the insertion portion and directly into the cervix to facilitate natural conception. For example, during and after ejaculation, the semen may be captured by a mesh or other features that uses capillary action or another mechanism to capture the semen. In some variations, the device may include a protective member to protect the semen and sperm from the vaginal environment (e.g., protect against the relative acidic environment in the vaginal environment).

An exemplary variation of a funneling conception aid is shown and described below with reference to FIG. 16.

Insertion Member

Figure 16:
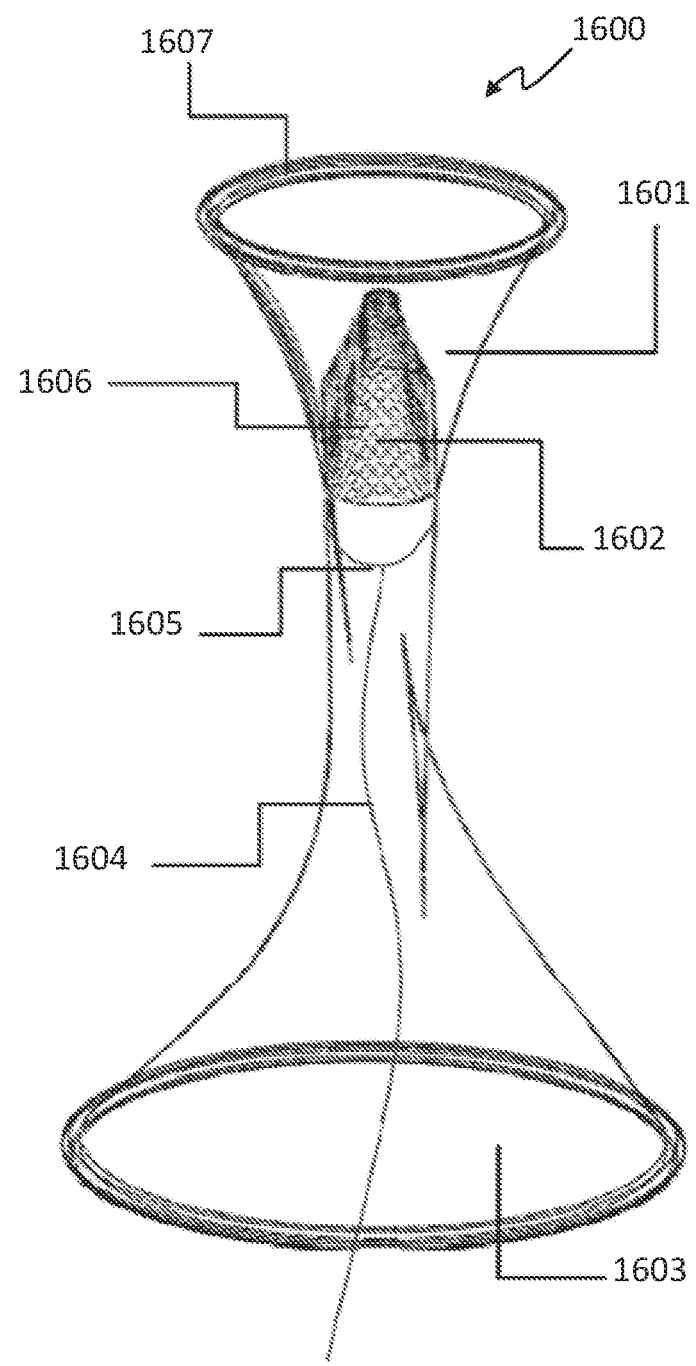
FIG. 16 depicts another variation of a conception aid having a funnel-like configuration.

FIG. 16 depicts another variation of a conception aid 1600 having a funnel-like configuration, which may also be used in assisting natural conception. As depicted in FIG. 16, an insertion member 1601 may be seen as defining a funnel-like configuration which may be inserted into the vaginal cavity of the female partner for positioning into proximity to the cervix such that the insertion member 1601 at least partially surrounds or envelops the cervix or is in proximity to the cervix. While illustrated as having a funnel-like configuration, other variations of the insertion member 1601 may take on other configurations. For example, the insertion member 1 may have the same or similar diameter throughout the length of the insertion member. Alternatively, instead of decreasing in diameter along its length, the diameter may increase along its length or the diameter may vary along its length in any number of configurations. In some variations, the insertion member 1601 may include a tubular and soft material. In some variations, the insertion member 1601 may include a soft material with features for easy insertion into the vaginal cavity. In some variations, the insertion member 1601 may be inserted into the vaginal cavity in a folded state and unfolded once it is inside the vaginal cavity.

In some variations, the insertion member 1601 may have features with higher surface friction defined on a portion of its outer surface for contact against the walls of the vaginal cavity to help ensure that the device does not slide out of the vaginal cavity easily. Such features may include any number of projections, protuberances, and so on, such as ribbed features, or even biocompatible adhesives which may help to temporarily adhere the outer surface of the insertion member 1601 to the vaginal walls.

Anchor Member

The anchor member 1607 may be attached to or form part of the insertion member 1601 such that anchor member 1607, in its deployed configuration, helps to ensure that the device remains within the vaginal cavity during the usage of the device. The anchor member 1601 may be arranged at a proximal end of the insertion member 1601. In some variations, the anchor member 1607 may include of a circular shaped part. In some variations, the anchor member 1607 may include one or more ribbed features. In some variations, the anchor member 1607 may include a cone-shaped, snout-shaped or cylinder-shaped part.

Regardless of the shape, the anchor member 1607 may be biased to extend outwardly relative to the structure such that when the anchor member 1607 remains positioned in a secure manner against the walls of the vaginal cavity and/or against the cervical opening.

Receptacle Member

While the insertion member 1601 may form a funnel-like structure which narrows from a first diameter to a second smaller diameter, the receptacle member 3 may extend from the insertion member 1601 to form a continuous structure which flares into a funnel-like structure from the second smaller diameter to a third larger diameter which is intended to be positioned into proximity to the vaginal opening. In some variations, rather than flaring into a funnel-like structure, the receptacle member 1603 may decrease in diameter along its length while in yet other variations, the diameter may remain the same or similar along the length of the receptacle member 1603. In some variations, the diameter may be varied along its length in any number of configurations.

The receptacle member 1603 may be accordingly positioned proximal to the vaginal opening and within the vaginal cavity or the distal opening may be positioned distal to the vaginal opening outside the vaginal cavity. In either case, the receptacle member 1603 may define a receiving cavity which is sized to receive the penis of the male partner during intercourse. In some variations, the receptacle member 1603 may include a tubular, flexible and/or soft material.

In some variations, the receptacle member 1603 may include one or more features with low friction to enable the penis to move into the receiving cavity. For example, the receptacle member 1603 may include a lubricated surface or may be used with a lubrication to facilitate movement of the penis within the receiving cavity.

In some variations, the receptacle member 3 may have features to minimize the likelihood of semen flowing out of the device upon the ejaculation and removal of the penis. In some variations, these are hydrophobic features. In some variations, these are ribs or other physical features that prevent the outward flow of the semen. In some variations, these may be hair-like or other features which use capillary action to prevent the outward flow of the semen.

Capturing Member

In some variations, the apparatus to assist natural conception includes at least one capturing member configured to capture semen. For example, as shown in FIG. 16, a capturing member 1602 may be positioned within the device lumen proximal to the receptacle member 1603 and extending at least partially into the insertion member 1601. In use, the capturing member 1602 may be used to capture as much semen as possible during and after ejaculation by the male into the receptacle member 1603. As the capturing member 1602 may extend proximally into the insertion member 1601, the capturing member 1602 may be maintained in a position to contact the cervix for as long as the device remains anchored within the vaginal cavity. By retaining the semen within the capturing member 1602, the volume of semen that may be transferred directly to the cervix is increased in order to facilitate the likelihood of conception occurring.

The capturing member 1602 may include one or more various features suitable for capturing semen. For example, in some variations, the capturing member 1602 may include a mesh structure. The mesh may be made of polymers, silicone or non-woven materials. The mesh may include pores smaller than, e.g., 1 cm, in diameter, or any suitable pore size. As another example, the capturing member 1602 may include one or more channels or lamella to capture the semen via capillary action or vacuum suction. As another example, the capturing member 1602 may include hair-like structures to capture the semen via capillary action. Furthermore, in some variations, the capturing member 1602 may include hydrophilic features. Additionally or alternatively, the capturing member 1602 may include, e.g., balloons, valves, pull-strings, elastic material or other mechanism to close the opening of the receptacle. In some variations, the capturing member 1602 may include a combination of the above variations.

Sealing Member

In some variations, the device may include at least one sealing member to seal the distal opening of the device after the semen is deposited on the device. The sealing member may, for example, configured to seal the capturing member to inhibit flow of semen distally into the receptacle member. In some variations, the sealing member may include, for example, one or more balloons, valves, pull-strings, elastic material, or the like.

For example, to facilitate the capturing and retention of the semen after ejaculation, a sealing member 1605 may be used to seal the capturing member 1602 to ensure that the semen does not flow out and back into the receptacle member 1603. It may include, for example, balloons, valves, pull-strings, elastic material and/or other mechanisms to close the capturing member 1602 from the receptacle member 1603 such that the semen can remain within the insertion member 1601 and within communication with the cervix.

In some variations, the sealing member 1605 may include a balloon that is inflated after ejaculation to seal the receptacle member 1603. In some variations, the sealing member 1605 may include a valve that seals the receptacle member 1603. In some variations, the sealing member 1605 may include a pull-string that seals the receptacle when tensile force is applied by the user. In some variations, the sealing member 1605 may include a radially closing member when a compressive or tensile force is applied by the user. In some variations, the sealing member 1605 may include a plug that is inserted by the user into the receptacle member to seal the device.

Guiding Member

In some variations, the apparatus to assist natural conception includes a guiding member configured to guide an insertion member into proximity to the cervical opening. For example, a guiding member may be optionally used by the user to guide the device and position the anchor member 1607 and insertion member 1601 into proximity to the cervical opening.

In some variations, the guiding member may include a semi-rigid or rigid shaft. Additionally or alternatively, in some variations, the guiding member may include one or more features within the insertion member 1601. The user may also use their fingers and these features to guide the device.

In some variations, the guiding member may include one or more features on the receptacle component. The user may use their fingers and these features to guide the device.

In some variations, the guiding member may have an overall shape of the device to naturally glide the device towards the cervical opening. One example of such shape is a conical shape that will naturally guide towards the cervical opening.

In some variations, the guiding member may be actuatable to conform and guide the sperm towards the cervical opening. Additionally or alternatively, in some variations, the enhancement member 1606 can mechanically vibrate, or pulsate periodically to vary the concentration of sperm cells near the cervical opening.

Enhancement Member

In some variations, the device may also include one or more enhancement members to enhance the sperm performance. For example, an enhancement member 1606 may be incorporated into the capturing member 1602 to help improve the likelihood of healthy motile sperms entering the cervical opening. The enhancement member 1606 may enable capacitation of the sperm by facilitating the entry of the sperm from the semen into the cervical mucus. Capacitation is a change to the state of the sperm when it is surrounded by the cervical mucus and/or leaving the semen. Capacitation leads to hyperactivity (increased motility) of the sperm cells, and which also allow the sperm cells to go through the acrosome reaction which is a step that is required for fertilization.

In some variations, the enhancement member 1606 increases sperm motility. For example, the enhancement member 1606 may include a combination of one or more of the following features, e.g., mesh, hair-like structure, lamella-like structure, channels, lubricants or some features with capillary action that interfaces between the semen and the cervical mucus to increase the percentage sperm that undergoes capacitation. In some variations, for example, the enhancement member 1606 may be the same structure as the capturing member 1602.

The enhancement member 1606 may include materials that slowly release neutralizing agents (e.g. pH modifying agents) in some of the members to aid the longevity of sperm. Additionally or alternatively, in some variations, the conception aid may include microenvironment control to enhance sperm motility, health, and capacitation. The microenvironment control can include coatings, fluids, or lubricant. In some variations, the microenvironment control is biodegradable.

Flagellated Cell Guiding Member

In some variations, the device may include guiding members to enhance the likelihood of motile sperm entering the cervical opening. These guiding members may guide motile sperm towards the cervical opening using mechanisms such as, but not limited to, channels, hair-like features, mesh, sperm-friendly liquid, and other features which uses capillary action to capture and guide sperm toward the cervical opening.

For example, the device may optionally include a cell guiding feature which may be defined, e.g., along the inner walls of the insertion member 1601. The cell guiding feature may generally include one or more flagellated cell guiding members which are configured to guide the sperm with flagella (tail structures) towards the cervical opening.

In some variations, the flagellated cell guiding members may be defined over the inner surface of the insertion member 1601 and/or a portion of the inner surface of the receptacle member 1603 so that sperm contained within ejaculate which may contact these inner surfaces can be guided towards the insertion member 1601 and into proximity to the cervix.

An example of the flagellated cell guiding member may include combinations of mesh, hair-like structure, lamella-like structure, channels, lubricants and/or features with capillary action that guides the sperm towards the cervical opening within the insertion member 1601.

In some variations, the cell guiding member encourages the movement of the sperm towards the cervical opening by providing pathways towards the cervical opening within the insertion member 1601.

In some variations, the cell guiding member encourages the movement of the sperm through the cervical opening and into the uterus by providing pathways through the cervical opening and into the uterus.

In some variations, the cell guiding member encourages the movement of the sperm towards the cervical opening within the insertion member 1601 by limiting the movement of the sperms in all direction except towards the cervical opening only.

In some variations, the cell guiding member may be actuatable to conform and guide the sperm towards the cervical opening within the insertion member 1601.

In some variations, the cell guiding member can include reversible actuations (e.g., vibrations, or other mechanical motions).

The device may further include one or more capacitating members to assist the capacitation of sperm by enabling sperm to swim out of seminal fluid into a capacitating medium. In other various variations, these capacitating members may include, for example, mesh structures, lamellar structures, hair-like structures, and/or channel like structures.

Removal Member

In some variations, the device may include a removal member to assist in the removal of the device after usage. For example, after ejaculation, the device may be maintained within the vaginal cavity for a period of time to allow for a sufficient amount of sperm to enter through the cervix within the insertion member 1601. However, once the device is to be removed, the user may simply grab onto a portion of the device and pull for removal from the vaginal cavity. Alternatively, a removal member 1604 may be incorporated into the device to facilitate removal of the device from the vaginal cavity after usage.

In some variations, the removal member 1604 may be configured to be attached to an interior portion of the device. For example, in some variations the removal member 1604 may include a long and flexible shaped mechanical member (e.g., strings, threads, etc.) that may be attached to an interior portion of the device such as between the insertion member 1601 and receptacle member 1603. The removal member 1604 may remain in place unobtrusively during intercourse but once the device is to be removed, the user may easily access the removal member 1604 manually to remove the device. With the removal member, the user may remove the entire device by sliding the device out of the vaginal cavity.

Although the conception aids described above are primarily described with respect to an application for assisting conception, in some variations the devices may be used for methods of use other than conception, such as, for example, delivery of drugs into the vagina, cervix, and uterus, or as a menstrual cup, as a contraception, or as a sexual stimulator. In some variations, the conception aid may include features for providing temperature control.

The applications of the devices and methods discussed above are not limited to uses for enabling natural conception but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

The foregoing description, for purposes of explanation, used specific nomenclature to provide a thorough understanding of the invention. However, it will be apparent to one skilled in the art that specific details are not required in order to practice the invention. Thus, the foregoing descriptions of specific variations of the invention are presented for purposes of illustration and description. They are not intended to be exhaustive or to limit the invention to the precise forms disclosed; obviously, many modifications and variations are possible in view of the above teachings. The variations were chosen and described in order to explain the principles of the invention and its practical applications, they thereby enable others skilled in the art to utilize the invention and various variations with various modifications as are suited to the particular use contemplated. It is intended that the following claims and their equivalents define the scope of the invention.

What is claimed is:

1. A conception aid, comprising:
a semen-collecting platform,
an extending member coupled to and extending from the platform, and
a flexible pocket structure;
wherein the flexible pocket structure is configured to engage with a vaginal wall of a vaginal canal after the conception aid is introduced to the vaginal canal;
wherein the flexible pocket structure is configured to flex in order to enable passage of a penis or an insemination device introduced into the vaginal canal,
wherein the flexible pocket structure is configured to re-engage with the vaginal wall after withdrawal of the penis or insemination device from the vaginal canal.

2. The conception aid according to claim 1, wherein the platform has a width tapering along a longitudinal axis between a proximal portion and a distal portion of the platform.

3. The conception aid according to claim 1, wherein the conception aid has a length such that when the platform is placed within the vaginal canal, a proximal portion of the platform is positioned proximate a cervical opening and at least a portion of the extending member is external to the vaginal canal.

4. The conception aid according to claim 1, wherein the extending member is angled relative to the platform.

5. The conception aid according to claim 1, wherein the extending member comprises a flared shape at a distal portion of the extending member.

6. The conception aid according to claim 1, wherein the platform comprises one or more capturing elements.

7. The conception aid according to claim 6, wherein one or more of the capturing elements are chosen from: one or more lateral ridges, one or more recesses, one or more longitudinal channels, one or more filaments, one or more holes configured to allow passage of sperm therethrough, one or more protrusions, and one or more bumps.

8. The conception aid according to claim 1, wherein the conception aid is curved along its longitudinal extent.

9. The conception aid according to claim 1, wherein the platform has a width tapering along a longitudinal axis between a proximal portion and a distal portion of the platform.

10. The conception aid according to claim 1, wherein the conception aid comprises a flexible material.

11. The conception aid according to claim 1, wherein the conception aid comprises silicone.

12. The conception aid according to claim 1, wherein the conception aid comprises an outer anchor.

13. The conception aid according to claim 12, wherein the outer anchor is configured to prevent the conception aid from slipping out of a desired position within the vaginal canal during intercourse or insertion of an insemination device.

14. The conception aid according to claim 1, wherein the conception aid is curved along its longitudinal extent, and the curvature is configured to retain semen.

15. The conception aid according to claim 1, wherein the conception aid is curved along its longitudinal extent, and the conception aid is configured to be flattened when the penis or insemination device is inside the vaginal canal, and the conception aid is configured to return to a curved shape when the penis or insemination device is withdrawn.

16. The conception aid according to claim 1, wherein the platform is circular, oval, rectangular, square, or a combination thereof.

17. The conception aid according to claim 1, wherein the conception aid comprises a flexible funnel-like structure.

18. The conception aid according to claim 1, wherein the conception aid comprises at least one sealing member to seal a distal opening of the platform after semen is deposited on the platform.

19. A conception aid, comprising:
a semen-collecting platform, and
an extending member coupled to and extending from the platform;
wherein the extending member is configured to extend distally from the platform such that the extending member may be manually grasped for guiding insertion of the platform into a vaginal canal;
wherein the extending member is configured for positioning a distal portion of the extending member outside of the entrance of the vaginal canal; and
wherein the extending member is configured to guide a penis or insemination device over the extending member towards the platform while the conception aid is in the vaginal canal.

20. The conception aid according to claim 19, wherein the conception aid is curved along its longitudinal extent, and the conception aid is configured to be flattened when the penis or insemination device is inside the vaginal canal, and the conception aid is configured to return to a curved shape when the penis or insemination device is withdrawn.

21. The conception aid according to claim 19, wherein the conception aid has a length such that when the platform is placed within the vaginal canal, a proximal portion of the platform is positioned proximate a cervical opening and at least a portion of the extending member is external to the vaginal canal.

* * * * *